US010813927B2

(12) United States Patent
Sebti et al.

(10) Patent No.: US 10,813,927 B2
(45) Date of Patent: *Oct. 27, 2020

(54) PLATINUM COMPOUNDS THAT INHIBIT CONSTITUTIVE STAT3 SIGNALING AND INDUCE CELL CYCLE ARREST AND APOPTOSIS OF MALIGNANT CELLS

(71) Applicants: H. LEE MOFFITT CANCER CENTER AND RESEARCH INSTITUTE, INC., Tampa, FL (US); UNIVERSITY OF CENTRAL FLORIDA RESEARCH FOUNDATION, INC., Orlando, FL (US)

(72) Inventors: Said M. Sebti, Tampa, FL (US); Nicholas J. Lawrence, Tampa, FL (US); James Turkson, Honolulu, HI (US)

(73) Assignees: H. LEE MOFFITT CANCER CENTER AND RESEARCH INSTITUTE, INC., Tampa, FL (US); UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/978,499

(22) Filed: May 14, 2018

(65) Prior Publication Data
US 2018/0256564 A1 Sep. 13, 2018

Related U.S. Application Data

(60) Continuation of application No. 14/947,786, filed on Nov. 20, 2015, now Pat. No. 9,968,599, which is a division of application No. 14/354,400, filed as application No. PCT/US2012/062272 on Oct. 26, 2012, now abandoned.

(60) Provisional application No. 61/551,737, filed on Oct. 26, 2011.

(51) Int. Cl.
*A61K 31/495* (2006.01)
*A61K 33/24* (2019.01)
*G01N 33/50* (2006.01)
*C07D 295/088* (2006.01)

(52) U.S. Cl.
CPC ............ *A61K 31/495* (2013.01); *A61K 33/24* (2013.01); *C07D 295/088* (2013.01); *G01N 33/5091* (2013.01)

(58) Field of Classification Search
CPC ............ C07D 295/088; G01N 33/5091; G01N 33/50; A61K 33/24; A61K 31/495
See application file for complete search history.

(56) References Cited

U.S. PATENT DOCUMENTS

| 7,888,395 B2 | 2/2011 | Luu et al. |
| 7,977,381 B2 | 7/2011 | Kay et al. |
| 8,455,543 B2 | 6/2013 | Kay et al. |
| 9,968,599 B2* | 5/2018 | Sebti .................. C07D 295/088 |
| 2003/0180823 A1 | 9/2003 | Leyland-Jones |
| 2005/0288365 A1 | 12/2005 | Kay et al. |
| 2009/0270418 A1 | 10/2009 | Sloss et al. |

OTHER PUBLICATIONS

Doadrio et al., Dep. Inorg. Chem., Fac. Pharm., Madrid Spain. Anales de Quimica., (1968-1979) (1977), 73(9-10), 1220-3.*
CAS Abstract of Doadrio et al., 73 Anales de Quimica (1968-1979), 1220-1223 (1977) (Year: 1977).*
Z. Liu et al., 306 Mol Cell Biochem, 115-122 (2007) (Year: 2007).*
R.A. Schwendener et al., 122 J Cancer Res Clin Oncol, 102-108 (1996) (Year: 1996).*
L. Byers et al., 15 Clin Cancer Res (2009) (Year: 2009).*
D. Bhasin et al., 18 Bioorganic & Medicinal Chemistry Letters (2008) (Year: 2008).*
D. Dykes et al., Murine L1210 and P388 Leukemias in Tumor Models in Cancer Research, (B. A. Teicher et al. ed., 2002). (Year: 2002).*
Tiekink, E.R.T. "Gold derivatives for the treatment of cancer" *Critical Rev. in Oncology/Hematology*, 2002, 42:225-248.
Türkyilmaz, M. et al. "1,1'-(Piperazine-1,4-diyl)dipropan-2-ol" *Acta Crystallographica*, 2011, E67:o1758.
Doadrio, A. et al. "On the preparation and antitumoral assay of some piperazine and antipiryne complex salts with hexachloroosmate (IV), hexachloroplatinate (IV), tetrachloroplatinate (II), tetrachloropalladate (II), and tetrachloroaurate (III) anions" *Anales de Quimica*, 1977, 73(9-10):1220-1223; Chemical Abstracts, vol. 89, No. 173626.
Akira, S. Roles of STAT3 defined by tissue-specific gene targeting. (2000) Oncogene 19, 2607-2611.
Allain, P. et al. Early Biotransformations of Oxaliplatin After Its Intravenous Administration to Cancer Patients. (2000) Drug. Metab. Dispos. 28, 1379-1384.
Becker, S. et al. Three-dimensional structure of the Stat3β homodimer bound to DNA. (1998) Nature 394, 145-151.
Bose, R. N. Biomolecular Targets for Platinum Antitumor Drugs. (2002) Mini. Rev. Med. Chem. 2, 103-111.
Bowman, T. et al. Stat3-mediated Myc expression is required for Src transformation and PDGF-induced mitogenesis. (2001) Proc. Natl. Acad. Sci. USA 98, 7319-7324.

(Continued)

*Primary Examiner* — Mark L Shibuya
*Assistant Examiner* — Ebenezer O Sackey
(74) *Attorney, Agent, or Firm* — Saliwanchik, Lloyd & Esenschenk

(57) ABSTRACT

The subject invention concerns a compound and compositions having activity as an inhibitor of Stat3 protein and methods of using the compound and compositions. In one embodiment, a compound of the invention has the structure shown in formula I, formula II, or formula III. The subject invention also concerns methods of using the compounds and compositions of the invention.

15 Claims, 12 Drawing Sheets

Specification includes a Sequence Listing.

(56) References Cited

OTHER PUBLICATIONS

Bowman, T. et al. STATs in oncogenesis. (2000) Oncogene 19, 2474-2488.
Bromberg, J. Signal transducers and activators of transcription as regulators of growth, apoptosis and breast development. (2000) Breast Cancer Res. 2(2), 86-90.
Bromberg, J.F. et al. Stat3 Activation Is Required for Cellular Transformation by v-src. (1998) Mol. Cell. Biol. 18, 2553-2558.
Bromberg, J.F. et al. Transcriptionally active Stat1 is required for the antiproliferative effects of both interferon α and interferon γ. (1996) Proc. Natl. Acad. Sci. USA 93, 7673-7678.
Bromberg, J.F. et al. Stat3 as an Oncogene. (1999) Cell 98, 295-303.
Buettner, R. et al. Activated STAT Signaling in Human Tumors Provides Novel Molecular Targets for Therapeutic Intervention. (2002) Clin. Cancer Res. 8, 945-954.
Catlett-Falcone, R. et al. Constitutive Activation of Stat3 Signaling Confers Resistance to Apoptosis in Human U266 Myeloma Cells. (1999) Immunity 10, 105-115.
Coffer, P.J. et al. The role of STATs in myeloid differentiation and leukemia. (2000) Oncogene 19, 2511-2522.
Darnell, J.E., Jr. Transcription Factors as Targets for Cancer Therapy. (2002) Nat. Rev. Cancer 2, 740-749.
Darnell, J.E., Jr. STATs and Gene Regulation. (1997) Science 277, 1630-1635.
Darnell, J.E., Jr. et al. Jak-STAT Pathways and Transcriptional Activation in Response to IFNs and Other Extracellular Signaling Proteins. (1994) Science 264, 1415-1421.
Epling-Burnette, P.K. et al. Inhibition of STAT3 signaling leads to apoptosis of leukemic large granular lymphocytes and decreased Mcl-1 expression. (2001) J. Clin. Invest. 107, 351-361.
Fukada, T. et al. Two Signals Are Necessary for Cell Proliferation Induced by a Cytokine Receptor gp130: Involvement of STAT3 in Anti-Apoptosis. (1996) Immunity 5, 449-460.
Garcia, R. et al. Constitutive activation of Stat3 by the Src and JAK tyrosine kinases participates in growth regulation of human breast carcinoma cells. (2001) Oncogene 20, 2499-2513.
Garcia, R. et al. Constitutive Activation of Stat3 in Fibroblasts Transformed by Diverse Oncoproteins and in Breast Carcinoma Cells. (1997) Cell Growth Diff. 8, 1267-1276.
Gouilleux, F. et al. Prolactin and Interleukin-2 Receptors in T Lymphocytes Signal through a MGF-STAT5-Like Transcription Factor. (1995) Endocrinology 136, 5700-5707.
Grandis, J.R. et al. Constitutive activation of Stat3 signaling abrogates apoptosis in squamous cell carcinogenesis in vivo. (2000) Proc. Natl. Acad. Sci. USA 97, 4227-4232.
Heudi, O. et al. Chemical instability and methods for measurement of cisplatin adducts formed by interactions with cysteine and glutathione. (2001) Int. J. Clin. Pharmacol. Ther. 39, 344-349.
Heudi, O. et al. Mechanisms of Reaction of $_L$-Methionine with Carboplatin and Oxaliplatin in Different Media: a Comparison with Cisplatin. (1999) Biopharm. Drug Dispos. 20, 107-116.
Hirano, T. et al. Roles of STAT3 in mediating the cell growth, differentiation and survival signals relayed through the IL-6 family of cytokine receptors. (2000) Oncogene 19, 2548-2556.
Hussain, S.F. et al. A Novel Small Molecule Inhibitor of Signal Transducers and Activators of Transcriptions 3 Reverses Immune Tolerance in Malignant Glioma Patients. (2007) Cancer Res. 67, 9630-9636.
Johnson, P.J. et al. Overexpressed pp60$^{c-src}$ Can Induce Focus Formation Without Complete Transformation of NIH 3T3 Cells. (1985) Mol. Cell. Biol. 5, 1073-1083.
Karras, J.G. et al. STAT3 Regulates the Growth and Immunoglobulin Production of BCL$_1$ B Cell Lymphoma through Control of Cell Cycle Progession. (2000) Cell. Immunol. 202, 124-135.
Kotenko, S.V. et al. Jak-Stat signal transduction pathway through the eyes of cytokine class II receptor complexes. (2000) Oncogene 19, 2557-2565.
Lin, T.S. et al. STAT signaling in the pathogenesis and treatment of leukemias. (2000) Oncogene 19, 2496-2504.

Mora, L.B. et al. Constitutive Activation of Stat3 in Human Prostate Tumors and Cell Lines: Direct Inhibition of Stat3 Signaling Induces Apoptosis of Prostate Cancer Cells. (2002) Cancer Res 62, 6659-6666.
Nielsen, M. et al. Inhibition of constitutively activated Stat3 correlates with altered Bcl-2/Bax expression and induction of apoptosis in mycosis fungoides tumor cells. (1999) Leukemia 13, 735-738.
Nielsen, M. et al. Constitutive activation of a slowly migrating isoform of Stat3 in mycosis fungoides: Tyrphostin AG490 inhibits Stat3 activation and growth of mycosis fungoides tumor cell lines. (1997) Proc. Natl. Acad. Sci. USA 94, 6764-6769.
Niu, G. et al. Gene Therapy with Dominant-negative Stat3 Suppresses Growth of the Murine Melanoma B16 Tumor in Vivo. (1999) Cancer Res. 59, 5059-5063.
Niu, G. et al. Constitutive Stat3 activity up-regulates VEGF expression and tumor angiogenesis. (2002) Oncogene 21, 2000-2008.
Oshiro, M.M. et al. Inhibition of JAK Kinase Activity Enhances Fas-mediated Apoptosis but Reduces Cytotoxic Activity of Topoisomerase II Inhibitors in U266 Myeloma Cells. (2001) Clin. Cancer Res. 7, 4262-4271.
Oyajobi, B.O. et al. Dual effects of macrophage inflammatory protein-1α on osteolysis and tumor burden in the murine 5TGM1 model of myeloma bone disease. (2003) Blood 102, 311-319.
Perez, J.M. et al. Antitumor and Cellular Pharmacological Properties of a Novel Platinum(IV) Complex: trans-[PtCl$_2$(OH)$_2$(Dimethylamine)(Isopropylamine)]. (2003) Mol. Pharmacol. 63, 933-944.
Persons, D.L. et al. Cisplatin-induced Activation of Mitogen-activated Protein Kinases in Ovarian Carcinoma Cells: Inhibition of Extracellular Signal-regulated Kinase Activity Increases Sensitivity to Cisplatin. (1999) Clin. Cancer. Res. 5, 1007-1014.
Sanchez-Perez, I. et al. Cisplatin induces a persistent activation of JNK that is related to cell death. (1998) Oncogene 16, 533-540.
Schindler, C. et al. Transcriptional Responses to Polypeptide Ligands: The JAK-STAT Pathway. (1995) Annu. Rev. Biochem. 64, 621-651.
Seidel, H.M. et al. Spacing of palindromic half sites as a determinant of selective STAT (signal transducers and activators of transcription) DNA binding and transcriptional activity. (1995) Proc. Natl. Acad. Sci. USA 92, 3041-3045.
Siddik, Z.H. Cisplatin: mode of cytotoxic action and molecular basis of resistance. (2003) Oncogene 22, 7265-7279.
Siddiquee, K. et al. Selective chemical probe inhibitor of Stat3, identified through structure-based virtual screening, induces antitumor activity. (2007) PNAS, 104(18):7391-7396.
Sinibaldi, D. et al. Induction of p21$^{WAF1-CIP1}$ and cyclin D1 expression by the Src oncoprotein in mouse fibroblasts: role of activated STAT3 signaling. (2000) Oncogene 19, 5419-5427.
Smithgall, T.E. et al. Control of myeloid differentiation and survival by Stats. (2000) Oncogene 19, 2612-2618.
Song, H. et al. A low-molecular-weight compound discovered through virtual database screening inhibits Stat3 function in breast cancer cells. (2005) PNAS 102(13), 4700-4705.
Song, J.I. et al. STAT signaling in head and neck cancer. (2000) Oncogene 19, 2489-2495.
Song, L. et al. Activation of Stat3 by receptor tyrosine kinases and cytokines regulates survival in human non-small cell carcinoma cells. (2003) Oncogene 22, 4150-4165.
Stark, G.R. et al. How Cells Respond to Interferons. (1998) Annu. Rev. Biochem. 67, 227-264.
Trynda-Lemiesz, L. et al. Human serum albumin: spectroscopic studies of the paclitaxel binding and proximity relationships with cisplatin and adriamycin. (2004) J. Inorg. Biochem. 98, 1851-1856.
Trynda-Lemiesz, L. et al. Effect of cis-, trans-diamminedichloroplatinum(II) and DBP on human serum albumin. (1999) J. Inorg. Biochem. 77, 141-146.
Turkson, J. STAT proteins as novel targets for cancer drug discovery. (2004) Expert Opin. Ther. Targets 8, 409-422.
Turkson, J. et al. STAT proteins: novel molecular targets for cancer drug discovery. (2000) Oncogene 19, 6613-6626.
Turkson, J. et al. Requirement for Ras/Rac1-Mediated p38 and c-Jun N-Terminal Kinase Signaling in Stat3 Transcriptional Activity Induced by the Src Oncoprotein. (1999) Mol. Cell. Biol. 19, 7519-7528.

(56) References Cited

OTHER PUBLICATIONS

Turkson, J. et al. Stat3 Activation by Src Induces Specific Gene Regulation and Is Required for Cell Transformation. (1998) Mol. Cell. Biol. 18, 2545-2552.

Turkson, J. et al. Novel peptidomimetic inhibitors of signal transducer and activator of transcription 3 dimerization and biological activity. (2004) Mol. Cancer Ther. 3, 261-269.

Turkson, J. et al. Phosphotyrosyl Peptides Block Stat3-mediated DNA Binding Activity, Gene Regulation, and Cell Transformation. (2001) J. Biol. Chem. 276, 45443-45455.

Turkson, J. et al. Inhibition of constitutive signal transducer and activator of transcription 3 activation by novel platinum complexes with potent antitumor activity. (2004) Mol. Cancer Ther. 3, 1533-1542.

Ueki, N. et al. Isolation and chromosomal assignment of a human gene encoding protein inhibitor of activated STAT3 (PIAS3). (1999) J. Human Genetics 44, 193-196.

Wagner, B.J. et al. The SIF binding element confers sis/PDGF inducibility onto the c-fos promoter. (1990) EMBO J. 9, 4477-4484.

Wang, G. et al. Molecular basis of cellular response to cisplatin chemotherapy in non-small cell lung cancer. (2004) Oncol. Rep. 12, 955-965.

Wang, T. et al. Regulation of the innate and adaptive immune responses by Stat-3 signaling in tumor cells. (2004) Nat. Med. 10, 48-54.

Yamauchi, K. et al. Phosphatidylinositol 3-Kinase Functions Upstream of Ras and Raf in Mediating Insulin Stimulation of c-fos Transcription. (1993) J. Biol. Chem. 268, 14597-14600.

Yu, C.-L., et al. Enhanced DNA-Binding Activity of a Stat3-Related Protein in Cells Transformed by the Src Oncoprotein. (1995) Science 269, 81-83.

Yu, H. et al. The STATs of Cancer—New Molecular Targets Come of Age. (2004) Nat. Rev. Cancer 4, 97-105.

Zhang, D. et al. STAT3 Participates in Transcriptional Activation of the C-reactive Protein Gene by Interleukin-6. (1996) J. Biol. Chem. 271, 9503-9509.

Zhang, Y. et al. Activation of Stat3 in v-Src-transformed Fibroblasts Requires Cooperation of Jak1 Kinase Activity. (2000) J. Biol. Chem. 275, 24935-24944.

\* cited by examiner

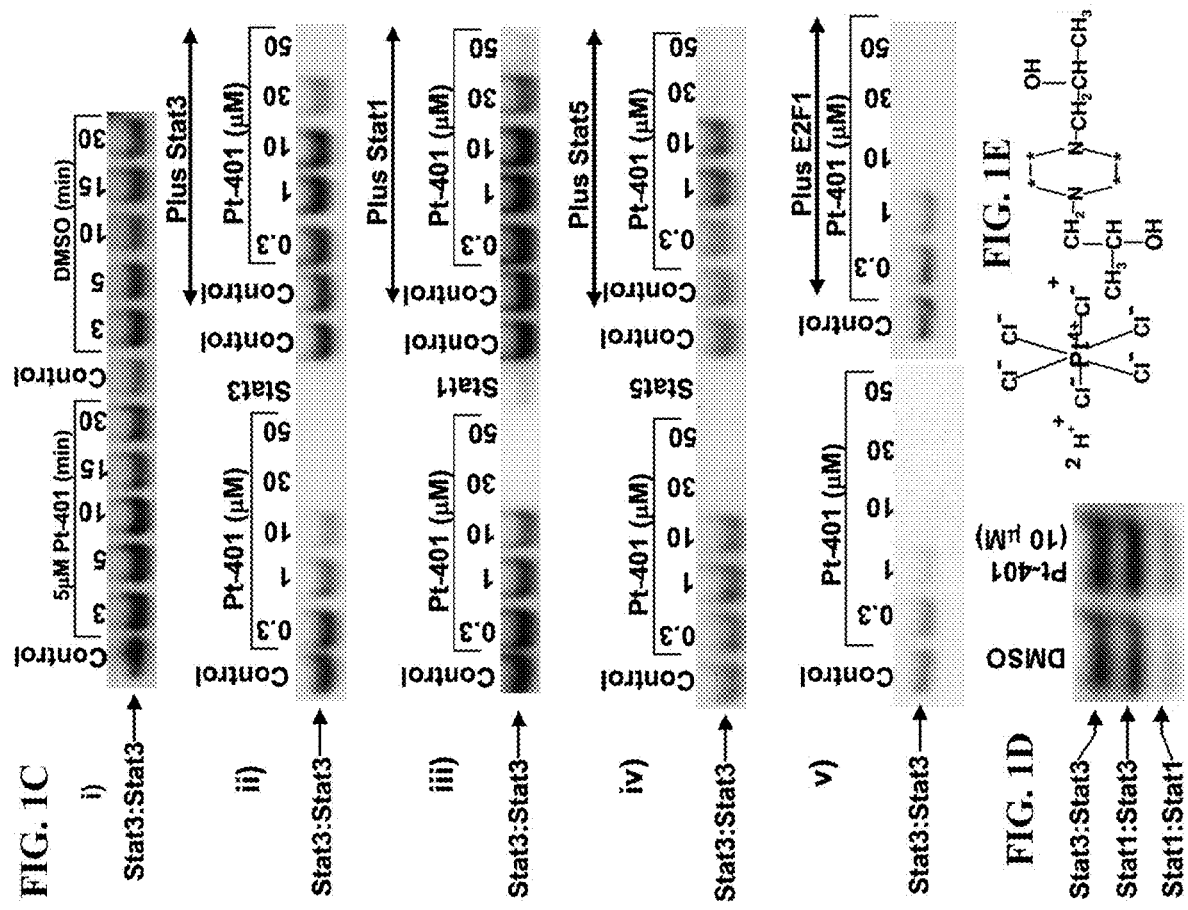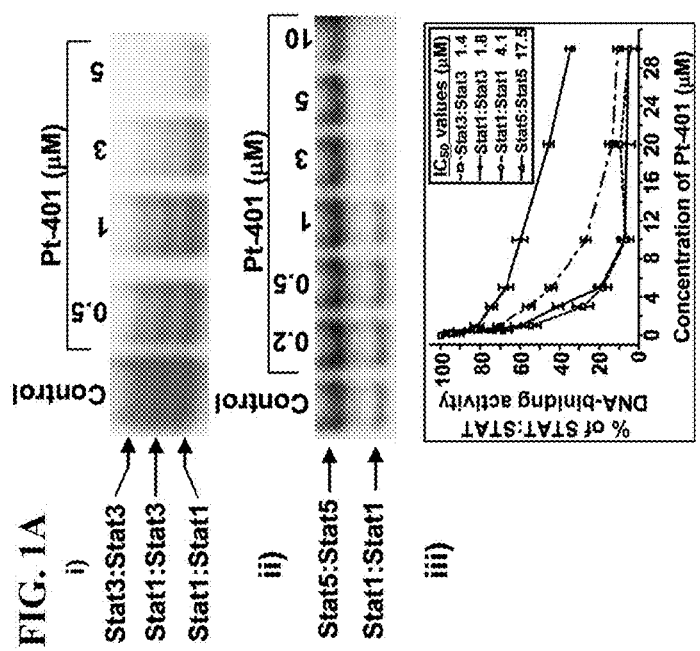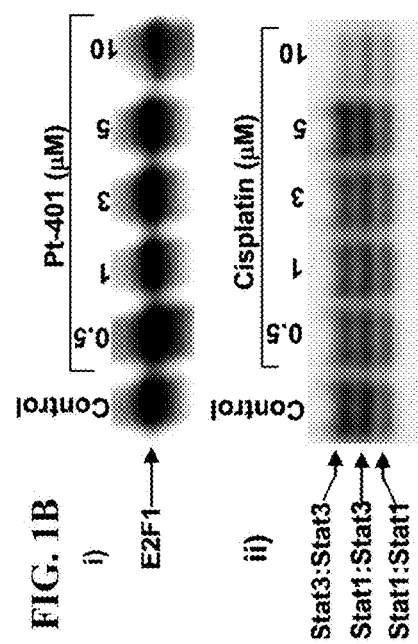

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial sequence
<220> FEATURE:
<223> OTHER INFORMATION: hSIE oligonucleotide probe

<400> SEQUENCE: 1
agcttcattt cccgtaaatc ccta                                              24

<210> SEQ ID NO 2
<211> LENGTH: 18
<212> TYPE: DNA
<213> ORGANISM: Artificial sequence
<220> FEATURE:
<223> OTHER INFORMATION: MGFe oligonucleotide probe

<400> SEQUENCE: 2
agatttctag gaattcaa                                                     18

<210> SEQ ID NO 3
<211> LENGTH: 20
<212> TYPE: DNA
<213> ORGANISM: Artificial sequence
<220> FEATURE:
<223> OTHER INFORMATION: Stat3 antisense oligonucleotide

<400> SEQUENCE: 3
gctccagcat ctgctgcttc                                                   20

<210> SEQ ID NO 4
<211> LENGTH: 20
<212> TYPE: DNA
<213> ORGANISM: Artificial sequence
<220> FEATURE:
<223> OTHER INFORMATION: control mismatch oligonucleotide

<400> SEQUENCE: 4
gctccaatac ccgttgcttc                                                   20
```

PLATINUM COMPOUNDS THAT INHIBIT CONSTITUTIVE STAT3 SIGNALING AND INDUCE CELL CYCLE ARREST AND APOPTOSIS OF MALIGNANT CELLS

CROSS-REFERENCE TO RELATED APPLICATIONS

The present application is a continuation of Ser. No. 14/947,786, filed Nov. 20, 2015, which is a divisional application of U.S. application Ser. No. 14/354,400, filed Apr. 25, 2014, now abandoned, which is the National Stage of International Application No. PCT/US2012/062272, filed Oct. 26, 2012, which claims the benefit of U.S. Provisional Application Ser. No. 61/551,737, filed Oct. 26, 2011, each of which is hereby incorporated by reference herein in its entirety, including any figures, tables, nucleic acid sequences, amino acid sequences, and drawings.

GOVERNMENT SUPPORT

This invention was made with government support under Grant No. CA55652 awarded by the National Cancer Institute. The government has certain rights in the invention.

The Sequence Listing for this application is labeled "2M68272.TXT" which was created on May 14, 2018 and is 1.38 KB. The entire contents of the sequence listing is incorporated herein by reference in its entirety.

BACKGROUND OF THE INVENTION

Cellular responses to growth factors and cytokines are characterized by the activation of signal transduction pathways, including the Signal Transducer and Activator of Transcription (STAT) family of cytoplasmic transcription factors (Darnell et al., 1994; Schindler et al., 1995; Darnell, 1997; Stark et al., 1998). Activation of STAT proteins is initiated upon their tyrosine phosphorylation, a key event in the formation of phosphotyrosine-SH2 (pTyr-SH2) interactions and the dimerization between two STAT monomers. In turn, dimers of STATs translocate to the nucleus and bind to specific DNA-response elements, thereby inducing the expression of genes essential for cellular responses. Normal physiological functions of STATs include regulation of cell proliferation, differentiation, development and apoptosis (reviewed in (Bromberg et al., 1996; Fukada et al., 1996; Kotenko et al., 2000; Smithgall et al., 2000; Hirano et al., 2000; Akira, 2000)).

In contrast to the tightly-regulated normal STAT signaling, constitutive activation of STAT proteins is frequently observed in human tumors (Turkson et al., 1998; Bromberg et al., 1998) and has been linked to tumor progression. Persistent activation of one STAT family member, Stat3, is detected in breast cancer, prostate cancer, head and neck squamous cell carcinoma, as well as in lymphomas and leukemias (Garcia et al., 1997; Nielsen et al., 1997; Catlett-Falcone et al., 1999; Nielsen et al., 1999; Bromberg, 2000; Grandis et al., 2000; Garcia et al., 2001; Epling-Burnette et al., 2001), reviewed in (Bowman et al., 2000a; Turkson et al., 2000; Song et al., 2000; Coffer et al., 2000; Lin et al., 2000; Buettner et al., 2002; Yu et al., 2004; Turkson, 2004a). In malignant cell lines and tumors that harbor constitutively-active Stat3, studies also reveal overexpression of Stat3-regulated genes encoding the anti-apoptotic proteins Bcl-xL and Mcl-1, the cell cycle regulators, Cyclin D1 and c-Myc, the angiogenesis factor, VEGF, as well as altered expression of immune-modulatory factors (Catlett-Falcone et al., 1999; Nielsen et al., 1999; Grandis et al., 2000; Epling-Burnette et al., 2001; Bowman et al., 2000b; Niu et al., 2002; Wang et al., 2004a). These abnormal gene expression changes contribute to dysregulated cell cycle progression, survival and angiogenesis, and to repressed host immune functions (reviewed in (Yu et al., 2004; Turkson, 2004b)). Thus, inhibition of abnormal Stat3 signaling is sufficient to repress the induction of these genes, resulting in cell cycle arrest and apoptosis of malignant cells (Catlett-Falcone et al., 1999; Grandis et al., 2000; Epling-Burnette et al., 2001; Niu et al., 1999), sensitization of tumor cells to chemotherapy-induced apoptosis (Oshiro et al., 2001), anti-tumor immune responses (Wang et al., 2004a), and tumor regression (Niu et al., 1999). Small-molecule inhibitors of Stat3, therefore, have the potential to impact tumors that harbor constitutively-active Stat3 with significant clinical benefits.

Previous studies have implicated signal transduction pathways in the antitumor activity of platinum complexes. Evidence shows that Cisplatin might modulate the mitogen-activated protein kinase family and the PI-3-kinase/Akt pathway (Sanchez-Perez et al., 1998; Persons et al., 1999; Bose, 2002; Siddik, 2003). Platinum complexes that inhibit Stat3 signaling and induce tumor regression have previously been reported (Turkson et al., 2004b).

BRIEF SUMMARY OF THE INVENTION

The subject invention concerns a compound and compositions having activity as an inhibitor of Stat3 protein and methods of using the compound and compositions. In one embodiment, a compound of the invention, designated herein as PLATINUM-401, has the structure shown in formula I:

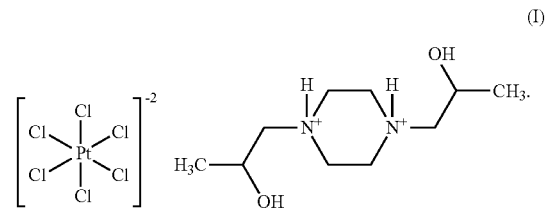

(I)

The compound in formula I is designated herein as Platinum-401. Analyses of in vitro DNA-binding activity and transcriptional regulation indicate that PLATINUM-401 interacts directly with Stat3, thereby inhibiting Stat3 binding to a consensus DNA response element and Stat3 transcriptional activity. Inhibition of constitutively-active Stat3 in malignant cells by PLATINUM-401 suppresses the induction of Stat3-regulated genes, including Bcl-xL and Cyclin D1. Studies in v-Src-transformed fibroblasts as well as in human and mouse tumor cell lines that harbor constitutive Stat3 activity reveal a $G_0/G_1$ cell cycle arrest and apoptosis following treatment with PLATINUM-401, which correlate with the inhibition of aberrant Stat3 signaling.

BRIEF DESCRIPTION OF THE DRAWINGS

FIGS. 1A-1E. Inhibition of in vitro Stat3 DNA-binding activity by a platinum complex. Nuclear extracts or cell lysates containing activated Stat1, Stat3 and Stat5, or E2F1 prepared from NIH3T3/hEGFR that are stimulated with EGF or Sf-9 insect cells that are infected with baculovirus expressing Stat1, Stat3, Stat5, or E2F1, respectively, were treated with or without the indicated concentrations of platinum complex, PLATINUM-401 or Cisplatin, for 30 min at room temperature prior to incubation with radiolabeled oligonucleotide probes, and subjected to EMSA analysis. (FIG. 1A) (i) Stat1 and Stat3 binding activities to hSIE probe, (ii) Stat1 and Stat5 binding activities to MGFe probe, and (iii) plot of % oligonucleotide probe-STAT:STAT complexes versus concentration of PLATINUM-401. Insert, $IC_{50}$ values for the inhibition of STAT:STAT DNA-binding activity; (FIG. 1B) (i) E2F1 binding activity to the dihydrofolate reductase promoter oligonucleotide probe, and (ii) Stat1 and Stat3 binding activities to hSIE probe; (FIG. 1C) PLATINUM-401 effect on the in vitro DNA-binding activity of Stat3, (i) 3-30 min after binding, or in the presence and absence of (ii) inactive Stat3 monomer, (iii) inactive Stat1 monomer, (iv) inactive Stat5 monomer, or (v) E2F1 protein; (FIG. 1D) Stat1 and Stat3 binding to PLATINUM-401-treated and untreated (DMSO) radiolabeled hSIE probe; and (FIG. 1E) structural formula of PLATINUM-401. Positions of STAT:STAT-DNA complexes in gel are labeled. In (A) to (C), the control lanes represent DMSO (vehicle)-treatment.

(FIG. 2A) DNA-binding activities for different Stat3 protein amounts in the presence of increasing concentrations of PLATINUM-401; (FIG. 2B) Levels of Stat3 binding to increasing amounts of hSIE oligonucleotide probe in the absence (control) and presence of PLATINUM-401; (FIG. 2C) Levels of Stat3 binding to hSIE oligonucleotide probe in the presence of increasing concentrations of PLATINUM-401; (FIG. 2D) Plots of hSIE-Stat3:Stat3 complex versus levels of hSIE oligonucleotide probe under different concentrations (0.3-2 µM) of PLATINUM-401; (FIG. 2E) Lineweaver-Burke analysis (double reciprocal plot) of hSIE-Stat3 complex versus levels of hSIE under different concentrations (0.3-2 µM) of PLATINUM-401. Positions of Stat3:Stat3-DNA complexes in gels are labeled.

(FIG. 3A) and (FIG. 3B) v-Src-transformed mouse fibroblasts that stably express Stat3-dependent (NIH3T3/v-Src/pLucTKS3) and Stat3-independent (NIH3T3/v-Src/pRLSRE) luciferase reporters or β-galactosidase (β-gal), as well as normal mouse fibroblast (NIH3T3) transiently transfected with pLucTKS3, pGL2-VEGF-Luc, NFkB-Luc or pLucSRE together with or without v-Src were treated with or without PLATINUM-401 for 48 h. Cytosolic extracts were then prepared from cells for luciferase and ß-gal activities measurements. Values are the means and S.D. of three to five independent assays; (FIG. 3C) and (FIG. 3D) Nuclear extracts or whole cell lysates were prepared from IL-6-stimulated normal mouse fibroblasts (NIH3T3) or their v-Src-transformed counterpart (NIH3T3/v-Src) that are treated with or without PLATINUM-401 for different times. Samples of equal total proteins were then subjected to in vitro DNA-binding activity and EMSA analysis or for SDS-PAGE and Western blot analysis for phosphorylated and total Stat3.

(FIG. 5A) EMSA analysis of Stat3 DNA-binding activity; (FIG. 5B) Graphical representations of quantified nuclear staining of Ki-67 proliferation index. Stat3:Stat3-DNA complexes in gels are labeled. The Ki-67 proliferation indexes were calculated as the percent positive tumor cells relative to the total number of cells. Ki67 values are representative of 3 independent assays.

(FIG. 7A) Normal NIH3T3 fibroblasts and their v-Src-transformed counterparts (NIH3T3/v-Src), human breast carcinoma cell lines (MDA-MB-453, MDA-MB-435, MDA-MB-468, and MDA-MB-231), human non-small cell lung cancer cell line (A549), human prostate cancer cell line (DU145), multiple myeloma 5TGM1 (mouse) and U266 (human) cell lines, mouse melanoma cell line (B16) and human pancreatic cancer cell line (Panc1) were all treated with or without PLATINUM-401 for 48 h and analyzed by TUNEL for DNA damage. For each cell line, the activated Stat3 status is indicated as (−), no constitutively-active Stat3 and (+), constitutively-active Stat3 (see FIG. 5A). Data are representative of 3 independent determinations; (FIG. 7B) Human breast cancer cell lines (MDA-MB-453, MDA-MB-468 and MDA-MB-435) were transfected with or without Stat3β or Stat3 antisense (Stat3AS), or were treated with or without Stat3 peptidomimetic inhibitor, ISS 610 (1 mM) or PLATINUM-401 (5 µM)). Forty-eight hours afterwards, cells were harvested and processed for TUNEL analysis; (FIG. 7C) The viral Src-transformed NIH3T3/v-Src fibroblasts were transfected with or without wild-type Stat3 (pRc/CMV Stat3 Flag) and treated with or without 5 µM PLATINUM-401 for 36 h. Cells were subsequently harvested for nuclear extracts preparation and Stat3 DNA-binding assay in vitro with EMSA analysis (left panel), or were processed for TUNEL analysis (right panel).

" (FIG. 8A) Detection of Cyclin D1; (FIG. 8B) Detection of Bcl-xL. Positions of Cyclin D1 and Bcl-xL proteins are shown. Beta-actin levels are shown for normalizing for equal total protein. Data are representative of 3 independent determinations.

BRIEF DESCRIPTION OF THE SEQUENCES

Figure 2D:
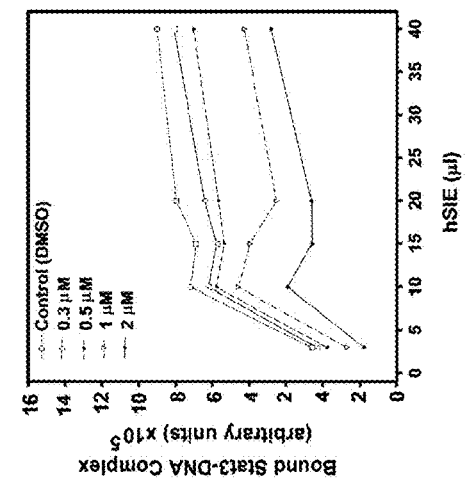
FIGS. 2A-2E. Kinetics of PLATINUM-401-mediated inhibition of in vitro Stat3 DNA-binding activity. Cell lysates containing activated Stat3 were incubated with radiolabeled hSIE probe for 30 min at room temperature in the presence or absence of PLATINUM-401 and then subjected to EMSA analysis.

SEQ ID NO:1 is an oligonucleotide that can be used as described herein.
SEQ ID NO:2 is an oligonucleotide that can be used as described herein.
SEQ ID NO:3 is an oligonucleotide that can be used as described herein.
SEQ ID NO:4 is an oligonucleotide that can be used as described herein.

DETAILED DESCRIPTION OF THE INVENTION

The subject invention concerns compounds and compositions disclosed herein having activity as inhibitors of Stat3 protein and methods of using the compounds and compositions. In one embodiment, a compound of the invention, designated herein as PLATINUM-401, has the structure shown in formula I:

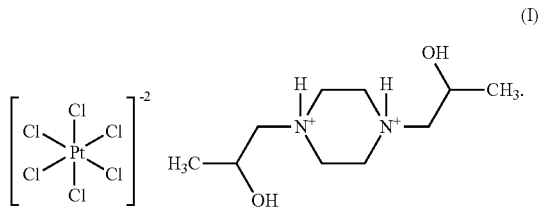

(I)

In another embodiment, a compound of the invention, designated herein as RPM 1581, has the structure shown in formula II (as a free base) or in formula III (as a salt):

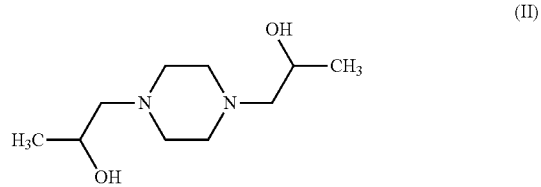

(II)

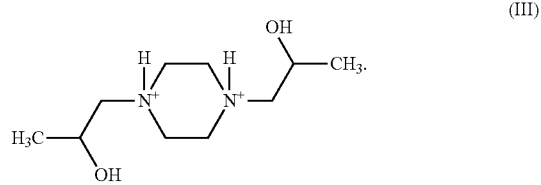

(III)

In one embodiment, the compound of formula III is provided as the chloride salt.

The subject invention also concerns compositions comprising a compound of formula I, or formula II, or formula III, and a carrier, buffer, and/or adjuvant.

The subject invention also concerns methods for treating a person or animal having a disorder or condition associated with aberrant or excessive Stat3 activity or interaction in a cell or decreased apoptosis of a cell, or a disorder or condition associated with inhibition or downregulation of apoptosis of a cell. In one embodiment, the disorder or condition is an oncological disorder or condition. In one embodiment, a person or animal is administered an effective amount of an inhibitor compound or composition of this invention. In one embodiment, the compound is the compound designated herein as PLATINUM-401 (formula I). In another embodiment, the compound is a chloroplatinic acid ($H_2PtCl_6$ or $K_2PtCl_6$, etc.). In still a further embodiment, the compound is the compound designated herein as RPM 1581 which can be in a free base (formula II) or salt form (e.g., formula III). In one embodiment, compounds and compositions of the invention can be used in combination with other Stat3 inhibitors, including, but not limited to, NSC 74859 (also known as S31-201; Siddiquee et al. (2007)), protein inhibitor of activated Stat3 (PIAS3) (Ueki et al. (1999)), WP1066 (Farzana Hussain et al. (2007)), or STA-21 (Song et al. (2005)). Oncological disorders include, but are not limited to, prostate cancer, head and neck squamous cell carcinoma, lymphomas, leukemias, and breast cancer.

The subject invention also concerns methods of inducing apoptosis in a cell. In one embodiment, a cell is contacted with an effective amount of an inhibitor compound or composition of this invention. In one embodiment, the compound is the compound designated herein as PLATINUM-401 (formula I). In another embodiment, the compound is a chloroplatinic acid ($H_2PtCl_6$ or $K_2PtCl_6$). In still a further embodiment, the compound is the compound designated herein as RPM 1581 which can be in a free base (formula II) or salt form (e.g., formula III). Cells can be any animal cell, such as a mammalian cell. Cells can be any mammalian cell, such as a human cell, canine cell, feline cell, or equine cell. In one embodiment the cell is a tumor cell, a cancer cell or a transformed cell. In one embodiment, the tumor or cancer cell is a breast cancer cell, prostate cancer cell, head and neck squamous cell carcinoma, lymphoma cell, leukemia cell, multiple myeloma cell, glioma cell, non-small cell lung cancer cell, melanoma cell, gastrointestinal stromal tumor cell, renal cell carcinoma, esophageal cell carcinoma, ovarian cancer cell, cervical cancer cell, or gastric cancer cell. In one embodiment, compounds and compositions of the invention can be used in combination with other Stat3 inhibitors, including, but not limited to, NSC 74859, PIAS3, WP1066, or STA-21.

The subject invention also concerns methods for inhibiting Stat3 interaction in a cell. In one embodiment, a cell is contacted with an effective amount of an inhibitor compound or composition of this invention. In one embodiment, the compound is the compound designated herein as PLATINUM-401 (formula I). In another embodiment, the compound is a chloroplatinic acid ($H_2PtCl_6$ or $K_2PtCl_6$). In still a further embodiment, the compound is the compound designated herein as RPM 1581 which can be in a free base (formula II) or salt form (e.g., formula III). Cells can be any animal cell, such as a mammalian cell. Cells can be any mammalian cell, such as a human cell, canine cell, feline cell, or equine cell. In one embodiment the cell is a tumor cell, a cancer cell or a transformed cell. In one embodiment, the tumor or cancer cell is a breast cancer cell, prostate cancer cell, head and neck squamous cell carcinoma, lymphoma cell, leukemia cell, multiple myeloma cell, glioma cell, non-small cell lung cancer cell, melanoma cell, gastrointestinal stromal tumor cell, renal cell carcinoma, esophageal cell carcinoma, ovarian cancer cell, cervical cancer cell, or gastric cancer cell. In one embodiment, compounds and compositions of the invention can be used in combination with other Stat3 inhibitors, including, but not limited to, NSC 74859, PIAS3, WP1066, or STA-21.

In some embodiments of the methods of the invention, the method further comprises a step to determine whether the disorder or condition is associated with aberrant or excessive Stat3 activity or interaction, or to verify that the cell aberrantly or constitutively expresses active Stat3. Preferably, this is carried out as a screening step prior to use of the compound. For example, in the treatment method, this determination can be made by measuring a level of Stat3 activity or interaction in a biological sample collected from the subject and comparing the measured level to a reference level of Stat3 activity or interaction. The biological sample will be appropriate and informative for the disorder or condition in question. For example, if the disorder or condition is a cancer, a sample of one or more of the cancer cells should be collected from the subject. The sample may be a bodily fluid or tissue sample, for example. In the apoptosis induction method, this determination can be made by measuring a level of Stat3 activity or interaction in the cell to be contacted or in another cell that is representative of the cell to be contacted with the compound (e.g., a cell in proximity to the target cell or a cell of the same type or apparently suffering from the same disorder or condition as the target cell). For example, if the cell is a tumor cell, one or more samples of the tumor may be taken to determine Stat3 status. Preferably, the determination is made prior to administering the compound to the subject or contacting the cell with the compound. As used herein, singular terms such as "cell" are inclusive of the plural form such as "cells". For example, the compound may be administered to a single cell or a plurality of cells. In some embodiments, the plurality of cells may be a tissue.

Methods for directly or indirectly measuring the level of Stat activity or interaction (such as Stat3 activity or interaction) are known in the art (see, for example, Turkson et al., 1998; Bromberg et al., 1998; Garcia et al., 1997; Nielsen et al., 1997; Catlett-Falcone et al., 1999; Nielsen et al., 1999; Bromberg, 2000; Grandis et al., 2000; Garcia et al., 2001; Epling-Burnette et al., 2001; Epling-Burnette et al., 2001; Bowman et al., 2000b; Niu et al., 2002; Wang et al., 2004a, which are each incorporated herein by reference in its entirety). Various Stat3 measurement methods known in the art and/or disclosed herein may be used to assess the Stat3 status of a cell or disorder/condition.

The subject invention also concerns a packaged dosage formulation comprising in one or more containers an inhibitor compound or composition of the invention. In one embodiment, a packaged dosage formulation comprises a compound designated herein as PLATINUM-401 (formula I). In another embodiment, the compound is a chloroplatinic acid ($H_2PtCl_6$ or $K_2PtCl_6$). In still a further embodiment, the compound is the compound designated herein as RPM 1581 which can be in a free base (formula II) or salt form (e.g., formula III). A packaged dosage formulation can optionally comprise in one or more containers a pharmaceutically acceptable carrier or diluent. A packaged dosage formulation can also optionally comprise, in addition to an inhibitor compound or composition of the invention, other Stat3 inhibitors, including, but not limited to, NSC 74859, PIAS3, WP1066, or STA-21.

In vivo application of the subject compound, and compositions containing it, can be accomplished by any suitable method and technique presently or prospectively known to those skilled in the art. The subject compound can be formulated in a physiologically- or pharmaceutically-acceptable form and administered by any suitable route known in the art including, for example, oral, nasal, rectal, and parenteral routes of administration. As used herein, the term parenteral includes subcutaneous, intradermal, intravenous, intramuscular, intraperitoneal, and intrasternal administration, such as by injection. Administration of the subject compound of the invention can be a single administration, or at continuous or distinct intervals as can be readily determined by a person skilled in the art.

The compound of the subject invention, and compositions comprising it, can also be administered utilizing liposome technology, slow release capsules, implantable pumps, and biodegradable containers. These delivery methods can, advantageously, provide a uniform dosage over an extended period of time. The compounds of the invention can also be administered in their salt derivative forms or crystalline forms.

Compounds of the subject invention can be formulated according to known methods for preparing physiologically acceptable compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds based on the weight of the total composition including carrier or diluent.

Compounds of the invention, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions of the invention to a cell comprises attaching the compounds to a protein or nucleic acid that is targeted for delivery to the target cell. U.S. Pat. No. 6,960,648 and Published U.S. Patent Application Nos. 20030032594 and 20020120100 disclose amino acid sequences that can be coupled to another composition and that allows the composition to be translocated across biological membranes. Published U.S. Patent Application No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly [bis(p-carboxyphenoxy) propane:sebacic acid] in a 20:80 molar ratio (as used in GLIADEL); chondroitin; chitin; and chitosan.

The subject invention also concerns methods for treating oncological disorders in a patient. In one embodiment, an effective amount of one or more compounds or compositions of the present invention is administered to a patient having an oncological disorder and who is in need of treatment thereof. Methods of the invention can optionally include identifying a patient who is or may be in need of treatment of an oncological disorder. The patient can be a human or other mammal, such as a primate (monkey, chimpanzee, ape, etc.), dog, cat, cow, pig, or horse, or other animals having an oncological disorder. Means for administering and formulating compounds for administration to a patient are known in the art, examples of which are described herein. Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include prostate cancer, head and neck squamous cell carcinoma, lymphomas, leukemias, and breast cancer.

Examples of cancers that can be treated according to the present invention are listed in Table 1.

TABLE 1

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult |
| Acute Myeloid Leukemia, Adult | (Primary) |
| Acute Myeloid Leukemia, Childhood | Hepatocellular (Liver) Cancer, Childhood |
| Adrenocortical Carcinoma | (Primary) |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, |
| Astrocytoma, Childhood Cerebral | Childhood |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sezary Syndrome |
| Brain Tumor, Childhood | Lymphoma, Hodgkin's, Adult |
| Breast Cancer | Lymphoma, Hodgkin's, Childhood |
| Breast Cancer, Childhood | Lymphoma, Hodgkin's During Pregnancy |
| Breast Cancer, Male | Lymphoma, Non-Hodgkin's, Adult |
| Bronchial Adenomas/Carcinoids, Childhood | Lymphoma, Non-Hodgkin's, Childhood |
| | Lymphoma, Non-Hodgkin's During Pregnancy |
| Burkitt's Lymphoma | Lymphoma, Primary Central Nervous System |
| Carcinoid Tumor, Childhood | |
| Carcinoid Tumor, Gastrointestinal | Macroglobulinemia, Waldenstrom's |
| Carcinoma of Unknown Primary | Malignant Fibrous Histiocytoma of Bone/Osteosarcoma |
| Central Nervous System Lymphoma, Primary | Medulloblastoma, Childhood |
| Cerebellar Astrocytoma, Childhood | Melanoma |
| Cerebral Astrocytoma/Malignant Glioma, Childhood | Melanoma, Intraocular (Eye) |
| Cervical Cancer | Merkel Cell Carcinoma |
| Childhood Cancers | Mesothelioma, Adult Malignant |
| Chronic Lymphocytic Leukemia | Mesothelioma, Childhood |
| Chronic Myelogenous Leukemia | Metastatic Squamous Neck Cancer with Occult Primary |
| Chronic Myeloproliferative Disorders | |
| Colon Cancer | Multiple Endocrine Neoplasia Syndrome, |

TABLE 1-continued

Examples of Cancer Types

| | |
|---|---|
| Colorectal Cancer, Childhood | Childhood |
| Cutaneous T-Cell Lymphoma, see Mycosis Fungoides and Sezary Syndrome | Multiple Myeloma/Plasma Cell Neoplasm |
| | Mycosis Fungoides |
| | Myelodysplastic Syndromes |
| Endometrial Cancer | Myelodysplastic/Myeloproliferative Diseases |
| Ependymoma, Childhood | Myelogenous Leukemia, Chronic |
| Esophageal Cancer | Myeloid Leukemia, Adult Acute |
| Esophageal Cancer, Childhood | Myeloid Leukemia, Childhood Acute |
| Ewing's Family of Tumors | Myeloma, Multiple |
| Extracranial Germ Cell Tumor, Childhood | Myeloproliferative Disorders, Chronic |
| | Nasal Cavity and Paranasal Sinus Cancer |
| Extragonadal Germ Cell Tumor | Nasopharyngeal Cancer |
| Extrahepatic Bile Duct Cancer | Nasopharyngeal Cancer, Childhood |
| Eye Cancer, Intraocular Melanoma | Neuroblastoma |
| Eye Cancer, Retinoblastoma | Non-Hodgkin's Lymphoma, Adult |
| Gallbladder Cancer | Non-Hodgkin's Lymphoma, Childhood |
| Gastric (Stomach) Cancer | Non-Hodgkin's Lymphoma During Pregnancy |
| Gastric (Stomach) Cancer, Childhood | Non-Small Cell Lung Cancer |
| Gastrointestinal Carcinoid Tumor | Oral Cancer, Childhood |
| Germ Cell Tumor, Extracranial, Childhood | Oral Cavity Cancer, Lip and Oropharyngeal Cancer |
| Germ Cell Tumor, Extragonadal | Osteosarcoma/Malignant Fibrous Histiocytoma of Bone |
| Germ Cell Tumor, Ovarian | |
| Gestational Trophoblastic Tumor | Ovarian Cancer, Childhood |
| Glioma, Adult | Ovarian Epithelial Cancer |
| Glioma, Childhood Brain Stem | Ovarian Germ Cell Tumor |
| Glioma, Childhood Cerebral Astrocytoma | Ovarian Low Malignant Potential Tumor |
| | Pancreatic Cancer |
| Glioma, Childhood Visual Pathway and Hypothalamic | Pancreatic Cancer, Childhood |
| | Pancreatic Cancer, Islet Cell |
| Skin Cancer (Melanoma) | Paranasal Sinus and Nasal Cavity Cancer |
| Skin Carcinoma, Merkel Cell | Parathyroid Cancer |
| Small Cell Lung Cancer | Penile Cancer |
| Small Intestine Cancer | Pheochromocytoma |
| Soft Tissue Sarcoma, Adult | Pineoblastoma and Supratentorial Primitive Neuroectodermal Tumors, Childhood |
| Soft Tissue Sarcoma, Childhood | |
| Squamous Cell Carcinoma, see Skin Cancer (non-Melanoma) | Pituitary Tumor |
| | Plasma Cell Neoplasm/Multiple Myeloma |
| Squamous Neck Cancer with Occult Primary, Metastatic | Pleuropulmonary Blastoma |
| | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive Neuroectodermal Tumors, Childhood | Primary Central Nervous System Lymphoma |
| | Prostate Cancer |
| T-Cell Lymphoma, Cutaneous, see Mycosis Fungoides and Sezary Syndrome | Rectal Cancer |
| | Renal Cell (Kidney) Cancer |
| | Renal Cell (Kidney) Cancer, Childhood |
| Testicular Cancer | Renal Pelvis and Ureter, Transitional Cell Cancer |
| Thymoma, Childhood | |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood |
| | Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult |
| | Sarcoma, Soft Tissue, Childhood |
| Unknown Primary Site, Cancer of, Childhood | Sarcoma, Uterine |
| | Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

For the treatment of oncological disorders, the compounds and compositions of this invention can be administered to a patient in need of treatment in combination with other antitumor or anticancer substances and/or with radiation and/or photodynamic therapy and/or with surgical treatment to remove a tumor. These other substances or treatments may be given at the same as or at different times from the compounds and compositions of this invention. For example, the compounds of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. In one embodiment, compounds and compositions of the invention can be used in combination with other Stat3 inhibitors, including, but not limited to, NSC 74859, PIAS3, WP1066, or STA-21.

The methods of the present invention can be used with humans and other animals. As used herein, the terms "subject", "patient", and "individual" refer to a human or non-human animal. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses. In one embodiment, the subject is a mammal. In one embodiment, the mammalian subject is a human. In another embodiment, the mammalian subject is a non-human mammal.

While inhibitor compounds of the invention can be administered to a subject or contacted with a cell as isolated compounds, these compounds can also be administered or contacted as part of a pharmaceutical composition. The subject invention thus further provides compositions comprising one or more compounds in association with at least one pharmaceutically acceptable carrier. The pharmaceutical composition can be adapted for various routes of administration, such as enteral, parenteral, intravenous, intramuscular, topical, subcutaneous, and so forth. Administration or contact can be continuous or at distinct intervals, as can be determined by a person of ordinary skill in the art. In cases where the cells are contacted in vivo, the cells are contacted by administration of the compound to a subject with the cells. The compound may be administered to a subject locally at a desired site of action or systemically.

The inhibitor compounds of the invention can be formulated according to known methods for preparing pharmaceutically useful compositions. Formulations are described in a number of sources which are well known and readily available to those skilled in the art. For example, Remington's Pharmaceutical Science (Martin 1995) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Therapeutic application of compounds and/or compositions containing them can be accomplished by any suitable therapeutic method and technique presently or prospectively known to those skilled in the art. Further, compounds and agents of the invention have use as starting materials or intermediates for the preparation of other useful compounds and compositions.

Compounds of the invention, and compositions thereof, may be locally administered at one or more anatomical sites, such as sites of unwanted cell growth (such as a tumor site or benign skin growth, e.g., injected or topically applied to the tumor or skin growth) or sites of fungal infection, optionally in combination with a pharmaceutically acceptable carrier such as an inert diluent. Compounds of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Compounds and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds of the invention may be applied in as a liquid or solid. However, it will generally be desirable to administer them topically to the skin as compositions, in combination with a dermatologically acceptable carrier, which may be a solid or a liquid. Compounds and compositions of the subject invention can be applied topically to a subject's skin to reduce the size (and may include complete removal) of malignant or benign growths, or to treat an infection site. Compounds of the invention can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The present invention also concerns pharmaceutical compositions comprising a compound of the invention in combination with a pharmaceutically acceptable carrier. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and compositions contemplated by the present invention can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and compositions of the present invention can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments may be given at the same as or at different times from the compounds of this invention. Examples of other chemotherapeutic agents contemplated within the scope of the invention include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of immunotherapeutic agents contemplated within the scope of the invention include, but are not limited to, alemtuzumab, cetuximab (ERBITUX), gemtuzumab, iodine 131 tositumomab, rituximab, trastuzumab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) The subject invention also concerns methods for treating an oncological disorder comprising administering an effective amount of a compound and/or composition of the invention prior to, subsequent to, and/or in combination with administration of a chemotherapeutic agent, an immunotherapeutic agent, a radiotherapeutic agent, or radiotherapy.

Examples of some chemotherapeutic agents that can be used according to the present invention are listed in Table 2.

TABLE 2

Examples of Chemotherapeutic Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |

TABLE 2-continued

Examples of Chemotherapeutic Agents

| | |
|---|---|
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |

TABLE 2-continued

Examples of Chemotherapeutic Agents

| | |
|---|---|
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

The subject invention also concerns methods for inhibiting Stat3 protein in a cell by contacting the cell with an effective amount of a compound or composition of the invention. In one embodiment, the cell is a human or mammalian cell, and can be a cancer or tumor cell or other cell that exhibits abnormal proliferation, survival, migration or differentiation. In one embodiment, the cell constitutively expresses or expresses elevated or abnormal levels of Stat3. In one embodiment, the tumor or cancer cell is a breast cancer cell, prostate cancer cell, head and neck squamous cell carcinoma, lymphoma cell, leukemia cell, multiple myeloma cell, glioma cell, non-small cell lung cancer cell, melanoma cell, gastrointestinal stromal tumor cell, renal cell carcinoma, esophageal cell carcinoma, ovarian cancer cell, cervical cancer cell, or gastric cancer cell. In one embodiment, the compound is the compound designated herein as PLATINUM-401 (formula I). In another embodiment, the compound is a chloroplatinic acid ($H_2PtCl_6$ or $K_2PtCl_6$). In still a further embodiment, the compound is the compound designated herein as RPM 1581 which can be in a free base (formula II) or salt form (e.g., formula III).

The subject invention also concerns methods for treating a person or animal (i.e., a subject) having a disorder associated with constitutive, abnormal, or elevated expression of Stat3 in a cell, wherein a therapeutically effective amount of a compound or composition of the invention is administered to the person or animal. The disorder can be one characterized, for example, by abnormal cell proliferation, cell survival, cell migration, and/or cell differentiation. In one embodiment, the compound is the compound designated herein as PLATINUM-401 (formula I). In another embodiment, the compound is a chloroplatinic acid ($H_2PtCl_6$ or $K_2PtCl_6$). In still a further embodiment, the compound is the compound designated herein as RPM 1581 which can be in a free base (formula II) or salt form (e.g., formula III).

Depending upon the disorder or disease condition to be treated, a suitable dose(s) may be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns methods for screening and/or diagnosing an oncological condition or disorder using a compound or composition of the invention wherein the condition or disorder is associated with constitutive active Stat3 expression or active Stat3 overexpression in a cell. In one embodiment, a cell is contacted with a PLATINUM-401 compound or composition and observing the cell for induction of apoptosis. Only cells expressing constitutively active Stat3 will exhibit induction of apoptosis upon exposure to PLATINUM-401 (formula I). In another embodiment, the compound is a chloroplatinic acid ($H_2PtCl_6$ or $K_2PtCl_6$). In still a further embodiment, the compound is the compound designated herein as RPM 1581 which can be in a free base (formula II) or salt form (e.g., formula III).

The subject invention also concerns kits comprising a compound or a composition comprising an inhibitor compound and/or agent of the invention in one or more containers. In one embodiment, the compound is the compound designated herein as PLATINUM-401 (formula I). In another embodiment, the compound is a chloroplatinic acid ($H_2PtCl_6$ or $K_2PtCl_6$). In still a further embodiment, the compound is the compound designated herein as RPM 1581 which can be in a free base (formula II) or salt form (e.g., formula III). Kits of the invention can optionally include pharmaceutically acceptable carriers and/or diluents. In one embodiment, a kit of the invention includes one or more other components, adjuncts, or adjuvants as described herein. In another embodiment, a kit includes one or more anti-cancer agents, such as those agents described herein. In one embodiment, a kit of the invention includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent of the invention is provided in the kit as a solid, such as a tablet, pill, or powder form. In another embodiment, a compound and/or agent of the invention is provided in the kit as a liquid or solution. In one embodiment, the kit comprises an ampoule or syringe containing a compound and/or agent of the invention in liquid or solution form. A kit of the invention can also optionally comprise, in addition to an inhibitor compound or composition of the invention, other Stat3 inhibitors, including, but not limited to, NSC 74859, PIAS3, WP1066, or STA-21.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient", "individual", and "subject" are used interchangeably and are intended to include such human and non-human species. Likewise, in vitro methods of the present invention can be carried out on cells of such human and non-human species.

The compound designated herein as PLATINUM-401 functions as a Stat3 inhibitor by directly interacting with the protein. The evidence indicates that PLATINUM-401 interacts with the Stat3 protein, both the inactive monomer and the activated dimer, and represses the Stat3 phosphotyrosine levels, DNA-binding activity and transcriptional regulation. Differences are evident in the modes of activity and selectivity between PLATINUM-401 and the widely used anti-tumor agent Cisplatin (Siddik, 2003; Wang et al., 2004b), which has no effect on Stat3 activity (Turkson et al., 2004b). By contrast, PLATINUM-401 blocks the binding of activated Stat3 to a specific DNA-response element. While the exact site(s) within the Stat3 protein that interacts with PLATINUM-401 is not yet known, preliminary evidence (data not shown) implicates cysteine residue(s). This is consistent with previous reports that Cisplatin and other platinum complexes interact with cysteine and methionine residues in serum albumin and γ-globulins (Bose, 2002; Trynda-Lemiesz et al., 1999; Allain et al., 2000; Trynda-Lemiesz and Luczkowski, 2004), forming thiol conjugates of platinum complexes (Allain et al., 2000; Heudi et al., 1999; Heudi et al., 2001). It is conceivable that such a modification in the Stat3 protein by PLATINUM-401 in turn occludes the binding of Stat3 to its consensus DNA-response element.

A non-competitive type inhibition by PLATINUM-401 was observed, supported by the reduced maximum DNA-binding activity of Stat3 following PLATINUM-401 treatment. The treatment of activated Stat3 with PLATINUM-401 also induces an apparent change in the protein's binding affinity for the consensus DNA sequence. Inferring from the known interactions of other platinum complexes with thiol-containing biological molecules (Siddik, 2003; Allain et al., 2000; Heudi et al., 1999; Heudi et al., 2001), the expected reaction of PLATINUM-401 with thiol groups of Stat3 would be irreversible. Those earlier studies and ours together suggest that PLATINUM-401 irreversibly modifies the Stat3 protein, thereby blocking the DNA-binding activity of the protein and subverting its transcriptional and biological functions. The lack of any PLATINUM-401 effect on Stat3 protein pre-bound to DNA suggests a shielding of the key amino acid(s) within the protein once the latter is first bound to DNA. This raises the possibility that both PLATINUM-401 and the DNA consensus sequence bind to the same region of Stat3 in the DNA-binding domain, or the Stat3 protein undergoes conformational changes upon binding to the DNA sequence, which restrict access to the key amino acid residue(s) and prevent interaction with PLATINUM-401. Indeed, the crystal structure of Stat3β dimer bound to DNA (Becker et al., 1998) shows that the protein is clamped around the DNA double helix, which may be sufficient to impede access by PLATINUM-401 to the DNA-binding domain.

Previous reports have established constitutively-active Stat3 as key to the dysregulated growth, survival, angiogenesis, and immune evasion that characterize tumorigenesis (Turkson and Jove, 2000; Yu and Jove, 2004). The biological effects of PLATINUM-401 are manifest in malignant cells harboring constitutively-active Stat3, including inhibition of Stat3-dependent transformation, as well as inhibition of cell growth with $G_0/G_1$ cell cycle arrest and apoptosis of malignant cells (Catlett-Falcone et al. 1999; Garcia et al., 2001; Bowman et al., 2000b; Turkson et al., 2004b). Thus, PLATINUM-401 inhibits Stat3-mediated induction of critical genes, including the cell cycle regulator, Cyclin D1, the anti-apoptotic Bcl-xL, as well as the pro-angiogenic VEGF, which are important in tumor processes (Catlett-Falcone et al. 1999; Niu et al., 2002; Bromberg et al., 1999; Sinibaldi et al., 2000).

In contrast to the DNA denaturation and the formation of platinum-DNA adducts by Cisplatin (Siddik, 2003; Perez et al., 2003), direct modification of DNA is not a key factor in the inhibition of Stat3 signaling and biological functions by PLATINUM-401. Findings herein show that the Stat3-binding integrity of the DNA response element is preserved following treatment of DNA with PLATINUM-401. Moreover, oligonucleotide melting and re-annealing analysis with agarose gel electrophoresis show a retention of the overall integrity of the PLATINUM-401-treated DNA response element (data not shown). The effects of PLATINUM-401 on Stat3 observed here also contrast that of Cisplatin and others that modulate the PI-3-kinase/Akt and MAPKs family pathways, which contribute to their biological effects (Sanchez-Perez et al., 1998; Persons et al., 1999; Bose, 2002; Siddik, 2003). The inventors do not observe effects of PLATINUM-401 on Stat3-independent transcriptional events.

EXEMPLIFIED EMBODIMENTS

Embodiment 1

A compound having the structure shown in formula I, formula II, or formula III:

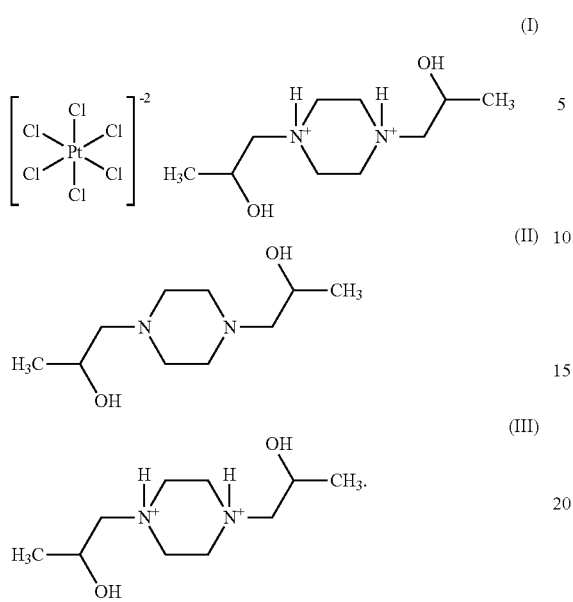

Embodiment 2

The compound of embodiment 1, wherein the compound has the structure of formula I.

Embodiment 3

The compound of embodiment 1, wherein the compound has the structure of formula II.

Embodiment 4

The compound of embodiment 1, wherein the compound has the structure of formula III.

Embodiment 5

The compound of embodiment 1, wherein the compound is a chloroplatinic acid ($H_2PtCl_6$ or $K_2PtCl_6$).

Embodiment 6

The compound of embodiment 1, wherein the compound is RPM 1581.

Embodiment 7

A composition comprising a compound of embodiment 1 and a carrier, buffer, adjuvant, a combination of two or more of the foregoing.

Embodiment 8

A method for treating a subject having a disorder or condition associated with aberrant or excessive Stat3 activity or interaction in a cell, comprising administering an effective amount of a compound of embodiment 1 to the subject.

Embodiment 9

The method of embodiment 8, wherein the disorder is an oncological disorder.

Embodiment 10

The method of embodiment 8 or 9, wherein the compound has the structure of formula I.

Embodiment 11

The method of embodiment 8 or 9, wherein the compound has the structure of formula II.

Embodiment 12

The method of embodiment 8 or 9, wherein the compound has the structure of formula III.

Embodiment 13

The method of embodiment 8 or 9, wherein the compound is a chloroplatinic acid ($H_2PtCl_6$ or $K_2PtCl_6$).

Embodiment 14

The method of embodiment 8 or 9, wherein the compound is RPM 1581.

Embodiment 15

The method of any preceding embodiment, wherein the method further comprises, determining that the disorder or condition is associated with aberrant or excessive Stat3 activity or interaction in a cell (e.g., prior to administering the compound).

Embodiment 16

The method of embodiment 15, wherein the determining comprises measuring a level of Stat3 activity or interaction in a biological sample collected from the subject and comparing the measured level to a reference level of Stat3 activity or interaction.

Embodiment 17

The method of any preceding embodiment, wherein the compound is administered to the subject in a composition comprising the compound and a carrier, buffer, adjuvant, or a combination of two or more of the foregoing.

Embodiment 18

The method of any preceding embodiment, wherein the subject is a mammal.

Embodiment 19

The method of embodiment 18, wherein the subject is a non-human mammal.

Embodiment 20

The method of embodiment 18, wherein the subject is human.

Embodiment 21

A method for inducing apoptosis in a cell aberrantly or constitutively expressing active Stat3, comprising contacting the cell with an effective amount of a compound of embodiment 1.

Embodiment 22

The method of embodiment 21, wherein the cell is a malignant cell.

Embodiment 23

The method of embodiment 21 or 22, wherein the compound has the structure of formula I.

Embodiment 24

The method of embodiment 21 or 22, wherein the compound has the structure of formula II.

Embodiment 25

The method of embodiment 21 or 22, wherein the compound has the structure of formula III.

Embodiment 26

The method of embodiment 21 or 22, wherein the compound is a chloroplatinic acid ($H_2PtCl_6$ or $K_2PtCl_6$).

Embodiment 27

The method of embodiment 21 or 22, wherein the compound is RPM 1581.

Embodiment 28

The method of any preceding embodiment, wherein the method further comprises, determining that the cell or a representative cell aberrantly or constitutively expresses active Stat3 (e.g., prior to contacting the cell with the compound).

Embodiment 29

The method of embodiment 28, wherein the determining comprises measuring a level of Stat3 activity or interaction in the cell or representative cell and comparing the measured level to a reference level of Stat3 activity or interaction.

Embodiment 30

The method of any preceding embodiment, wherein the contacting comprises contacting the cell with a composition comprising the compound and a carrier, buffer, adjuvant, or a combination of two or more of the foregoing.

Embodiment 31

The method of any preceding embodiment, wherein the contacting is carried out in vitro.

Embodiment 32

The method of any one of embodiments 23 to 24, wherein the contacting is carried out in vivo.

Embodiment 33

The method of embodiment 30, wherein the contacting comprises administering the effective amount of the compound to a human.

Embodiment 34

A method for screening and/or diagnosing an oncological condition or disorder using a compound of embodiment 1, wherein the condition or disorder is associated with constitutive active Stat3 expression or active Stat3 overexpression in a cell, wherein the method comprises contacting a cell with a compound of embodiment 1 and observing the cell for induction of apoptosis.

Embodiment 35

A kit comprising a compound of embodiment 1 in one or more containers.

Materials and Methods

Cells and Reagents

Src-transformed NIH3T3/v-Src, NIH3T3/v-Src/pLucTKS3, NIH3T3/v-Src/pRLSRE, and NIH3T3/hEGFR fibroblasts, human breast cancer (MDA-MB-231, MDA-MB-435, MDA-MB-453, and MDA-MB-468), human prostate cancer (DU145), multiple myeloma U266 (human) and 5TGM1 (mouse), mouse melanoma (B16), and human pancreatic cancer (Pancl) cell lines have all been previously described (Catlett-Falcone et al., 1999; Garcia et al., 2001; Niu et al., 1999; Johnson et al., 1985; Yu et al., 1995; Turkson et al., 2001; Mora et al., 2002; Oyajobi et al., 2003). Cells were grown in Dulbecco's modified Eagle's medium (DMEM) containing 5% iron-supplemented bovine calf serum, with or without G418 or zeocin, or in RPMI containing 10% heat-inactivated fetal bovine serum. The recombinant human epidermal growth factor (rhEGF) and interleukin-6 (IL-6) were obtained from R & D Systems (Minneapolis, Minn.).

Plasmids

The Stat3 reporter, pLucTKS3, Stat3-dependent VEGF promoter-driven reporter (pGL2-VEGF-Luc), and the Stat3-independent reporter, pLucSRE, all of which drive the expression of firefly luciferase, as well as the Stat3-independent pRLSRE *renilla* luciferase reporter have all been previously described (Turkson et al., 1998; Niu et al., 2002; Turkson et al., 1999). The pLucTKS3 plasmid harbors seven copies of a sequence corresponding to the Stat3-specific binding site in the promoter of the human C-reactive protein gene (Zhang et al., 1996). The pRLSRE and pLucSRE, each contains two copies of the serum response element (SRE) from the c-fos promoter (Turkson et al., 1998; Yamauchi et al., 1993), subcloned into the *renilla* (pRL-null) or firefly (pGL2) luciferase reporter, respectively (Promega, Madison, Wis.). The plasmid pNFκB-Luc is firefly luciferase obtained from Strategene (La Jolla, Calif.). The plasmid pRc/CMV Stat3 Flag tagged was a gift from Dr. James Darnell, Jr. (The Rockefeller University).

Cytosolic Extract Preparation and Luciferase Assays

Cytosolic extract preparation from fibroblasts and luciferase assays were previously described (Turkson et al., 1998; Turkson et al., 1999). Briefly, after two washes with PBS and equilibration for 5 min with 0.5 ml of PBS-0.5 mM EDTA, cells were scraped off the dishes and the cell pellet was obtained by centrifugation (4,500×g, 2 min, 4° C.).

Cells were resuspended in 0.4 ml of low-salt HEPES buffer (10 mM HEPES [pH 7.8], 10 mM KCl, 0.1 mM EGTA, 0.1 mM EDTA, 1 mM phenylmethylsulfonyl fluoride (PMSF), and 1 mM dithiothreitol (DTT)) for 15 min, lysed by the addition of 20 µl of 10% Nonidet P-40 (NP-40), and centrifuged (10,000×g, 30 s, 4° C.) to obtain the cytosolic supernatant, which was used for luciferase assays (Promega) measured with a luminometer. Cytosolic lysates were prepared from recombinant baculovirus-infected Sf-9 cells for Stat3 protein, as previously described (Zhang et al., 2000). Briefly, cultured dishes of Sf-9 cells were washed twice with ice-cold 1×PBS and then PBS containing 1 mM sodium orthovanadate. Cells were then lysed in 1% NP-40 lysis buffer (50 mM HEPES [pH 7.9], 150 mM NaCl, 1% NP-40, 20 mM NaF, 1 mM sodium orthovanadate, 1 mM tetrasodium pyrophosphate, 1 mM DTT, 0.5 mM PMSF, 2 mM EGTA, 2 mM EDTA, 0.1 µM aprotinin, 1 µM leupeptin, and 1 µM antipain) on ice for 10 min, and centrifuged (13,000×g, 30 s, 4° C.) to obtain lysate.

Nuclear Extract Preparation and Gel Shift Assays

Nuclear extract preparation from NIH3T3 stimulated by rhIL-6, NIH3T3/hEGFR stimulated by rhEGF, v-Src-transformed fibroblasts (NIH3T3/v-Src) or tumor cell lines and electrophoretic mobility shift assay were carried out as previously described (Turkson et al., 1998; Garcia et al., 1997; Yu et al., 1995). The $^{32}$P-labeled oligonucleotide probes used are hSIE (high affinity sis-inducible element from the c-fos gene, m67 variant, 5'-AGCTTCATTTCCCG-TAAATCCCTA) (SEQ ID NO:1) that binds Stat1 and Stat3 (Garcia et al., 1997; Wagner et al., 1990) and MGFe (mammary gland factor element from the bovine β-casein gene promoter, 5'-AGATTTCTAGGAATTCAA) (SEQ ID NO:2) for Stat1 and Stat5 binding (49, 50). Except where indicated, inhibitor compound was pre-incubated with the nuclear extract for 30 min at room temperature prior to incubation with radiolabeled probe.

Western Blot—

Whole-cell lysates were prepared in boiling sodium dodecyl sulfate (SDS) sample-loading buffer to extract total proteins from the cytoplasm and nucleus. Equivalent amounts of total cellular protein were electrophoresed on an SDS-10% polyacrylamide gel and transferred onto nitrocellulose membranes. Probing of nitrocellulose membranes with primary antibodies and detection of horseradish peroxidase-conjugated secondary antibodies by enhanced chemiluminescence (Amersham, Piscataway, N.J.) were performed as previously described (Garcia et al., 2001; Turkson et al., 2004b; Zhang et al., 2000). The probes used were anti-Cyclin D1 (Cell Signaling Technologies, Beverly, Mass.), anti-Bcl-xL (Cell Signaling Technologies), and anti-β-Actin (Sigma-Aldrich, St. Louis, Mo.) antibodies.

Soft-Agar Colony Formation Assays

Colony formation assays were carried out in six-well dishes as previously described (Turkson et al., 1999). In brief, each well contained 1.5 ml of 1% agarose in DMEM as the bottom layer, and 1.5 ml of 0.5% agarose in DMEM containing 4000 or 6000 NIH3T3/v-Src or NIH3T3/v-Ras fibroblasts, respectively, as the top layer. Treatment with PLATINUM-401 was initiated 1 day after seeding cells by adding 75-100 µl of medium with or without compound, and repeated every three days, until large colonies were evident. Colonies were quantified by staining with 20 µl of 1 mg/ml iodonitrotetrazolium violet, incubating at 37° C. overnight and counting the next day.

Cell Proliferation and TUNEL Assays

Proliferating cells were first treated with or without PLATINUM-401 for up to 48 h. A portion of cells were harvested for BrdU incorporation following the manufacturer's (BD Biosciences Pharmingen, San Diego, Calif.) instructions and analyzed by flow cytometry. Harvested cells were also analyzed for apoptosis via detection of TdT-mediated dUTP nick-end labeling (TUNEL) assay using Apoptosis Detection Systems Fluorescein according to the manufacturer's (Roche, Indianapolis, Ind.) instructions.

Oligonucleotides and Plasmids Transfections.

The Stat3 antisense (5'-<u>GCTCC</u>AGCATCTGCT<u>GCTTC</u>-3') (SEQ ID NO:3) or control mismatch oligonucleotides (5'-<u>GCTCC</u>AATACCCGTT<u>GCTTC</u>-3') (SEQ ID NO:4) were synthesized using phosphorothioate chemistry and were synthesized with 2'-Omethoxyethyl modification of the five terminal nucleotides (underlined; (Mora et al., 2002; Karras et al., 2000)) to increase stability. Transfections of Stat3AS and plasmids were carried out with Lipofectamine 2000 (LF) according to the manufacturer's instructions (Invitrogen, Carlsbad, Calif.). Briefly, cells were seeded at 1-2×10$^6$ cells/10-cm tissue-culture plates 18 h before transfection. Immediately before transfection, cells were washed once with PBS. Cells were transfected with luciferase reporters (4 µg) in the presence or absence of v-Src (4 µg), or were transfected with Stat3β (4 µg) or pRC/CMV Stat3 Flag (4 µg). Stat3AS transfections were carried out LF alone, or with LF/Stat3 antisense oligonucleotides, or LF/Stat3 mismatch oligonucleotides (final concentration of the oligonucleotides was 250 nM). After 2-3 h, the transfection medium was aspirated and cells washed with PBS before fresh medium added containing 10% FBS was added. Forty-eight h after transfection cells were washed and cytosolic lysates prepared for luciferase, as previously described (Turkson et al., 1998; Turkson et al., 1999), or processed for TUNEL staining.

Immunohistochemistry

The indirect peroxidase-antiperoxidase test was performed on cytospins prepared from cell lines (control and treated). After inhibition of endogenous peroxidase with 0.3% H$_2$O$_2$ and methanol for 30 min, slides were rinsed in PBS [pH 7.4], treated for 30 min with 1.5% normal goat serum and then incubated for 1 h with primary antibody against Ki-67 (Vector Laboratories, Burlingame, Calif.) at 1:100 dilution. Slides were then rinsed in PBS and incubated with biotinylated secondary antibody (Vector Laboratories) at 1:200 dilution for 30 min. Following washing with PBS, the preparations were further incubated in avidin-peroxidase conjugate (Vector Laboratories). The visualization was carried out with 3,3'-diaminobenzidine (Vector Laboratories) for 2 min. For microscopic evaluation, the preparations were counterstained with hematoxylin and mounted. Negative controls consisted of replacement of the primary antibody with PBS. The presence of Ki-67 nuclear staining was calculated as percent positive tumor cells in relation to the total number of cells.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1-Identification of PLATINUM-401 as an Inhibitor of Stat3 DNA-Binding Activity Compounds from the NCI 2000 diversity set were screened for inhibition of Stat3 signaling in an in vitro DNA-binding activity assay based on analysis by electrophoretic mobility shift assay (EMSA). A platinum (IV)

complex, PLATINUM-401 (NSC 295558) (FIG. 1E), was identified as a potent inhibitor of Stat3 and was further characterized for its anti-Stat3 properties. In the in vitro DNA-binding activity assay, nuclear extracts of equal total protein containing active Stat1, Stat3 and Stat5 were pre-incubated with different concentrations of PLATINUM-401 for 30 min prior to incubation with a [$^{32}$P]-labeled oligonucleotide, the m67 high affinity sis-inducible element (hSIE) probe that binds Stat1 and Stat3, or the mammary gland factor element (MGFe) that binds Stat1 and Stat5. Samples were then subjected to EMSA. Results show that the presence of PLATINUM-401 in nuclear extracts leads to a dose-dependent reduction in the levels of DNA-binding activity of Stat3:Stat3 homodimer (FIG. 1A (i), upper band), Stat1:Stat3 heterodimer (FIG. 1A (i), intermediate band), and to a lesser extent of Stat1:Stat1 homodimer (FIG. 1A (i) and (ii), lower band). In contrast, EMSA analysis shows that the presence of PLATINUM-401 does not significantly affect the level of DNA-binding activity of Stat5:Stat5 dimer (FIG. 1A (ii), upper band). These results indicate that PLATINUM-401 selectively disrupts Stat3 over Stat1 (IC$_{50}$ values of 1.4 µM and 4.1 µM, respectively, FIG. 1A (iii)), consistent with our previous findings with other platinum (IV) complexes (Turkson et al., 2004b).

In control studies, the effect of PLATINUM-401 was evaluated on the DNA-binding activity of the E2F1 protein that is unrelated to STATs. Analysis by EMSA shows that pre-incubation with PLATINUM-401 of cell lysates containing E2F1 prior to incubation with a [$^{32}$P]-labeled dihydrofolate reductase (DHFR) promoter sequence as probe has no significant effect on the DNA-binding activity (FIG. 1B (i)). In another control study, Cisplatin was similarly evaluated on DNA-binding activities of STAT proteins and E2F1 and has no detectable effect on the DNA-binding activities of Stat1, Stat3 and Stat5 (FIG. 1B (ii)) and data not shown), or of E2F1 (data not shown) DNA-binding activity in vitro. These findings together suggest that the effect of PLATINUM-401 is selective for Stat3, and that it is not a general phenomenon of all platinum compounds to inhibit the activities of transcription factors.

Example 2-Lack of Effect of PLATINUM-401 on STAT Proteins Pre-Bound to DNA

To further characterize the disruption of in vitro Stat3 DNA-binding activity by PLATINUM-401, the sequence of addition of reagents during the DNA-binding activity assay was changed to determine how it affects the kinetics of PLATINUM-401-mediated inhibition. Nuclear extracts containing activated Stat3 were first incubated with radiolabeled hSIE probe for 30 min (to allow prior Stat3 binding to the oligonucleotide probe) followed by the addition of PLATINUM-401 for an additional 3-30 min, and then subjected to EMSA analysis. PLATINUM-401 fails to disrupt Stat3 DNA-binding activity when the protein is first bound to the DNA-response element probe (FIG. 1C (i), lanes 1-6 compared to control lanes 7-12). These findings indicate that DNA-bound Stat3 protein is occluded from inhibition by PLATINUM-401, suggesting that the Stat3 region required for interaction with PLATINUM-401 is already bound to DNA. By contrast, EMSA analysis shows that the simultaneous addition of PLATINUM-401 and the hSIE oligonucleotide probe to nuclear extracts containing activated Stat3 protein results in inhibition of Stat3 DNA-binding activity (data not shown), as observed in FIG. 1A, suggesting that Stat3 has a higher preference for PLATINUM-401 over hSIE.

Example 3-Interaction of PLATINUM-401 with STAT Proteins

Because the evidence suggested a possible interaction of activated Stat3 dimers with PLATINUM-401, the inventors asked the question whether inactive STAT monomer proteins could do the same. To address this, cell lysates of inactive STAT monomer proteins were added to that of activated Stat3 and the mixture was pre-incubated with PLATINUM-401 for 30 min prior to incubation with radiolabeled hSIE probe and EMSA analysis. While inactive STAT monomer proteins do not bind the DNA response element or alter the binding of activated Stat3 dimer protein to DNA (FIG. 1C (ii), lane 7), if they could interact with PLATINUM-401 the inventors reasoned that they would lower the concentration of the PLATINUM-401 and thereby diminish the extent of PLATINUM-401-mediated inhibition on the DNA-binding activity of activated Stat3 dimer.

Consistent with this possibility, EMSA analysis shows that the presence of inactive Stat3 monomer significantly diminishes the inhibitory effects of PLATINUM-401 on activated Stat3 DNA-binding activity (FIG. 1C (ii), compare lanes 10-13 to 2-5). Indeed, the presence of the inactive Stat3 monomer protein completely restores the DNA-binding activity of active Stat3 dimers that was hitherto abolished by the 1-10 µM PLATINUM-401 (FIG. 1C (ii), lanes 11-12 vs. 3-40) and results in partial recovery of the active Stat3 DNA-binding activity that is otherwise completely disrupted at high (30 µM) concentrations of PLATINUM-401 (FIG. 1C (ii), lanes 13 vs. 5). However, at the level of protein present in the mixture, the inactive Stat3 monomer is insufficient to impact higher concentrations (50 µM) of PLATINUM-401 and hence no recovery of active Stat3 DNA-binding activity is observed (FIG. 1C, last lane). These findings together show that monomer Stat3 interacts with PLATINUM-401 and titrates it out, thereby reducing the levels that are available to inhibit active Stat3. The interaction of PLATINUM-401 with Stat3 protein is independent of the activation status of the protein.

Similar observations were made when inactive Stat1 monomer was present in the mixture (FIG. 1C (iii), compare lanes 8-12 to lanes 1-6), suggesting that PLATINUM-401 also interacts with Stat1 protein. In contrast, inactive Stat5 monomer or a non-STAT-related protein, E2F1, failed to significantly influence PLATINUM-401's effect on Stat3 DNA-binding activity (FIG. 1C (iv), compare lanes 8-14 to lanes 1-6 and FIG. 1C (v), compare lanes 7-12 to lanes 1-6).

To investigate the possibility that PLATINUM-401 might alter the integrity of the hSIE oligonucleotide probe that is used in the DNA-binding activity studies and thereby inhibit Stat3 binding, the oligonucleotide was first treated with PLATINUM-401 for 30 min. Pre-treated oligonucleotide was then radiolabeled and tested for its ability to bind to activated Stat3 in vitro. EMSA analysis reveals that the PLATINUM-401 pre-treated radiolabeled hSIE probe bound activated protein similarly to the non-treated oligonucleotide probe (FIG. 1D, lanes 1 vs. 2), indicating that the pre-PLATINUM-401 treatment of oligonucleotide has no observable effect on the ability of the Stat3-responsive DNA sequence to bind to activated Stat3 in vitro. While PLATINUM-401 was in direct contact with the oligonucleotide probe during the pre-treatment stage and prior to radiolabeling of the probe, it is unlikely to have been retained with the oligonucleotide probe following purification of the probe and therefore would not have come into contact with Stat3 protein at the time of the in vitro DNA-binding assay. Thus, under the conditions of the in vitro DNA-binding assay, PLATINUM-401 does not directly alter the binding properties of the Stat3-responsive DNA element, suggesting the DNA element may not directly interact with the PLATINUM-401.

Example 4-Kinetics of PLATINUM-401-Mediated Inhibition of Stat3 DNA-Binding Activity To further explore the interaction of PLATINUM-401 with Stat3 protein, the levels of activated Stat3 protein and radiolabeled hSIE oligonucleotide probe were varied during the in vitro DNA-binding assay and the extent of PLATINUM-401-mediated inhibition was determined. EMSA analysis shows that in vitro Stat3 DNA-binding activity increases with increasing protein amounts (FIG. 2A, lanes 1, 6 and 11). At low (1 µg) protein amount, the presence of PLATINUM-401 causes a strong and a dose-dependent decrease in the level of Stat3 DNA-binding activity (FIG. 2A, lanes 2-5), consistent with FIG. 1A (i). In contrast, there is diminished effect of PLATINUM-401 on Stat3 DNA-binding activity at higher (2-3 µg) protein levels (FIG. 2A lanes 6-15), suggesting that increasing the Stat3 protein amount overcomes the inhibitory effects of PLATINUM-401 (FIG. 2A, compare lanes 8-10, 13-15 to lanes 3-5). The apparent restoration of Stat3 DNA-binding activity at greater protein amounts suggests high levels of residual active Stat3 protein (in excess of the amount that interacted with PLATINUM-401), which in turn bound the probe. Altogether, the findings (FIGS. 1 and 2A) indicate that PLATINUM-401 interacts with Stat3 protein and thereby inhibits Stat3 DNA-binding activity.

Figure 2E:
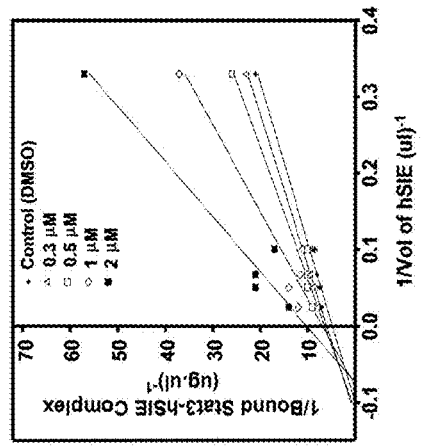
Figure 2A:
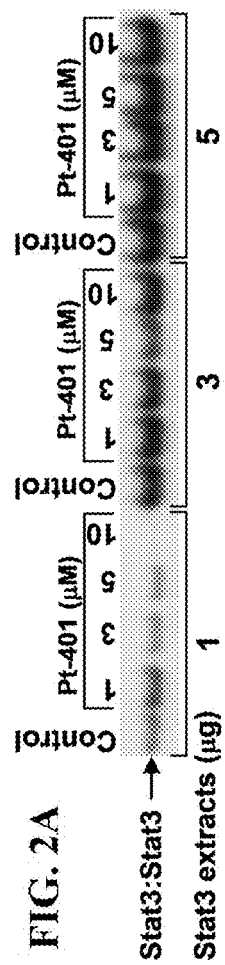
Figure 2B:
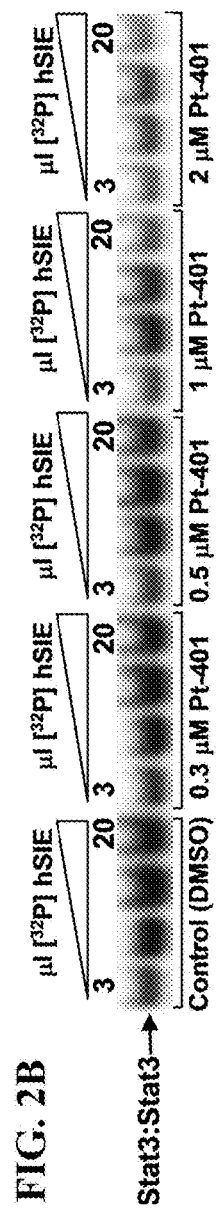
Figure 2C:
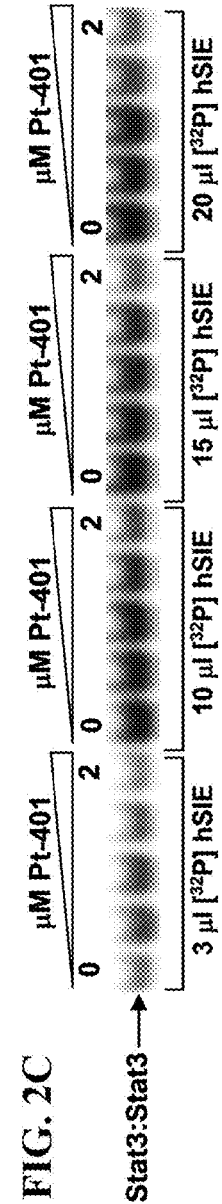

For the same protein amount, results further show that increasing the level of radiolabeled hSIE probe results in an increased level of in vitro DNA-binding activity of Stat3 (FIG. 2B, FIG. 2C, lanes 1, 6, 11 and 16, and FIG. 2D), until a maximum DNA-binding activity is reached at higher levels of hSIE (a saturation or plateau phase in the plot of Stat3-DNA complex versus amount of hSIE) (FIG. 2D). In the presence of PLATINUM-401, however, the maximum binding levels (plateau phase) attained are diminished, particularly at high (1-2 µM) concentrations of PLATINUM-401 (FIG. 2B, FIG. 2C and FIG. 2D), suggesting that increasing probe levels fail to overcome the inhibitory effect of higher concentrations of PLATINUM-401. Instead, varying degrees of saturation of Stat3 DNA-binding activity are observed with increasing probe levels under high (0.3-2 µM) PLATINUM-401 concentrations (FIG. 2D). Thus, increasing the oligonucleotide probe levels does not restore the maximum DNA-binding activity that is expected for any given amount of protein at different PLATINUM-401 concentrations (1 µM and higher) (FIG. 2D). A Lineweaver-Burke (double reciprocal) plot of Stat3-DNA complex versus concentration of hSIE suggests the inhibitory effect on Stat3 DNA-binding activity by PLATINUM-401 displays non-competitive type kinetics (FIG. 2E), with apparent changes in affinity and maximum binding levels.

Figure 3A:
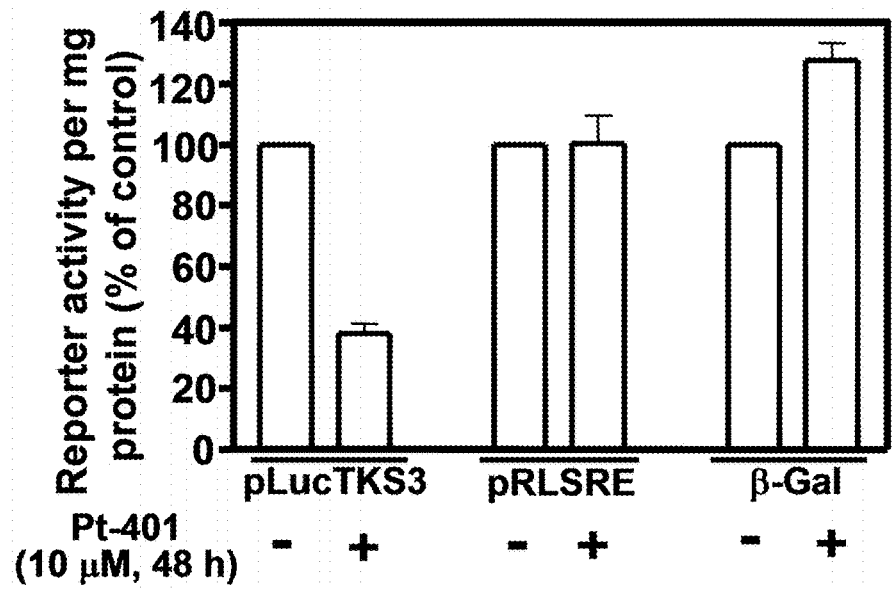
FIGS. 3A-3D. Inhibition of Stat3-mediated gene expression by PLATINUM-401.
Figure 3B:
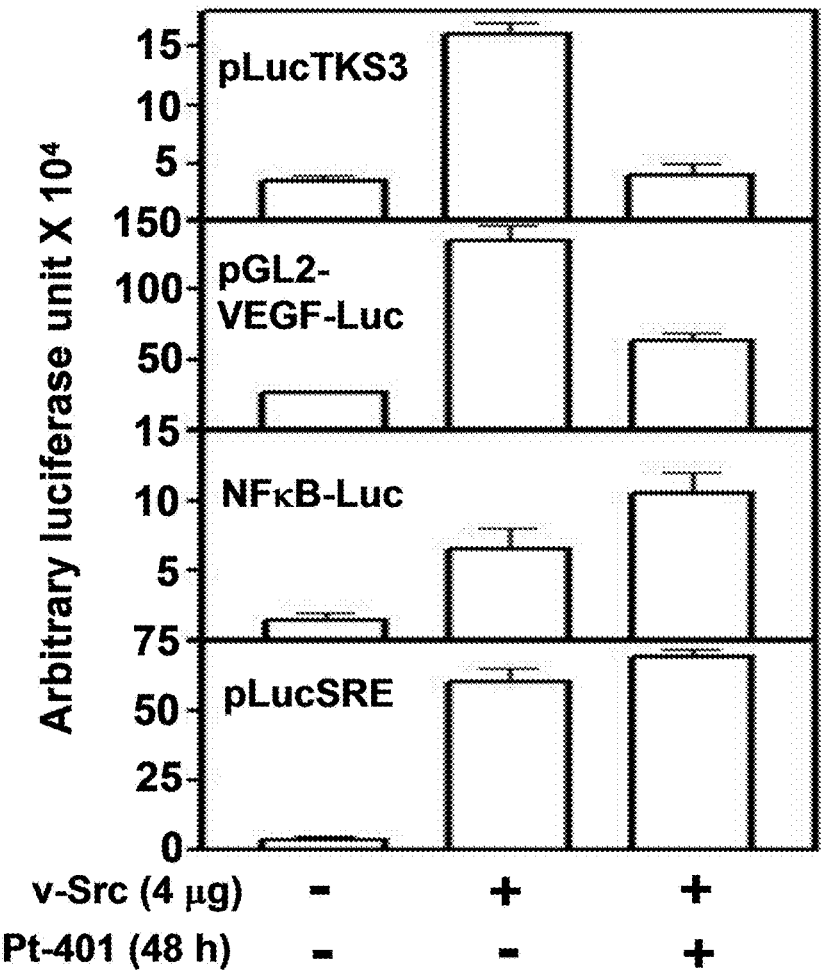
Figure 3C:
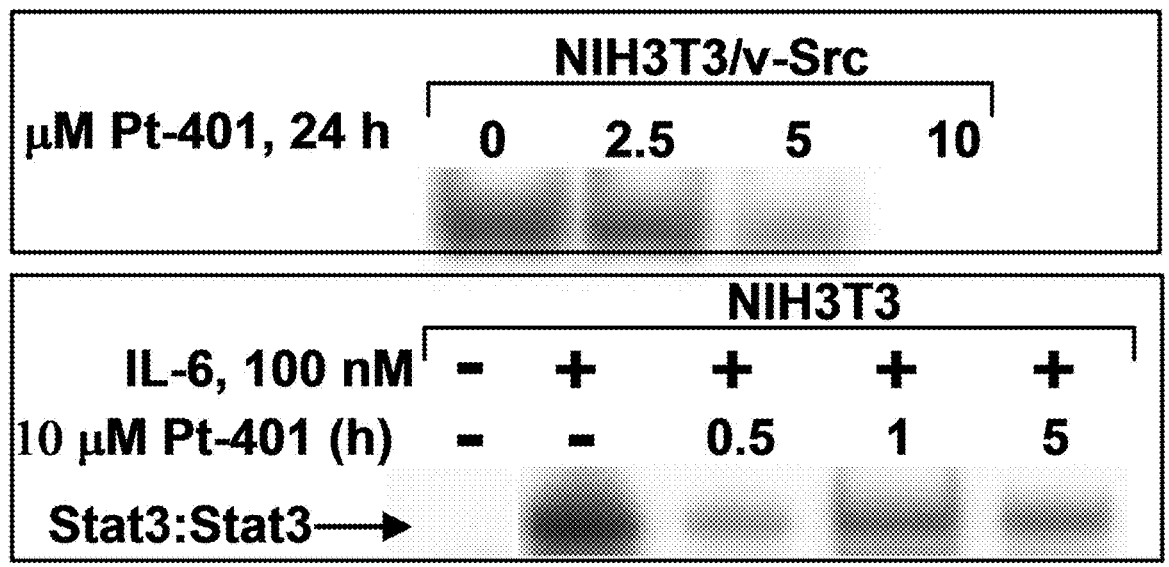
Figure 3D:
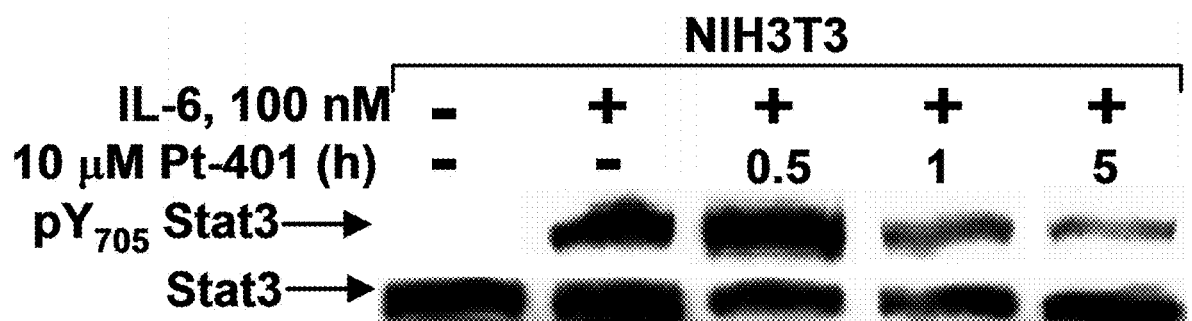
Figure 4:
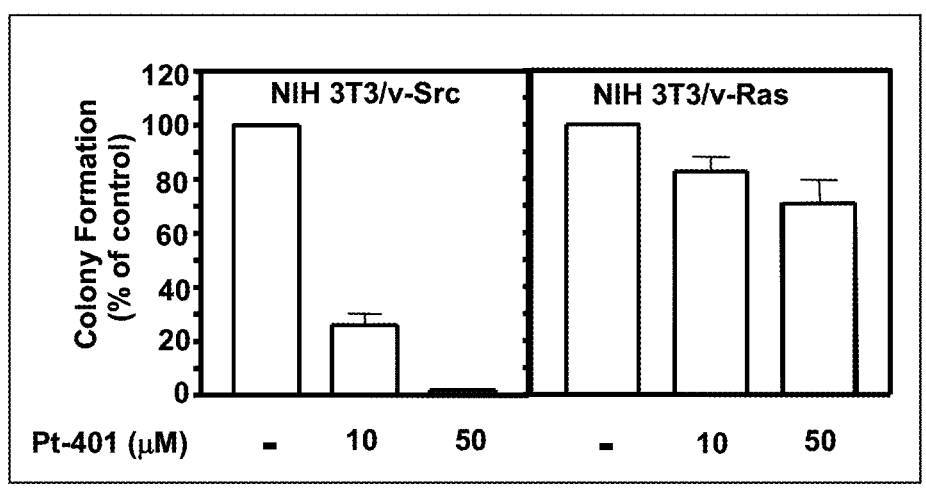
FIG. 4. Abrogation of Stat3-dependent viral Src transformation. Viral Src-transformed fibroblasts (NIH3T3/v-Src) and their Ras-transformed counterparts (NIH3T3/v-Ras) were seeded in soft agar and growing cells were treated every 2-3 days with or without the indicated concentrations of PLATINUM-401 until large colonies were evident. Number of colonies of cells in soft agar were counted and expressed as % of control (non-treated) cells. Values are the mean and S.D. of the three independent assays.

Example 5-PLATINUM-401 Selectively Blocks Intracellular Stat3 Signaling and Stat3-Mediated Transformation To further investigate the activities of PLATINUM-401, the inventors treated malignant cells and measured effects on Stat3 signaling. In stable cell lines (NIH3T3/v-Src/pLucTKS3 and NIH3T3/v-Src/RLSRE) harboring constitutively-active Stat3 and overexpressing Stat3-dependent firefly (pLucTKS3) and Stat3-independent renilla (pRLSRE) luciferase reporters (Turkson et al., 2001), PLATINUM-401 strongly suppresses the induction of Stat3-dependent reporter but not the Stat3-independent luciferase reporter or the induction of the β-galactosidase (β-gal) in the v-Src-transformed fibroblasts expressing 3-gal vector (FIG. 3). Similar results were obtained in transient transfection studies of mouse NIH3T3 fibroblasts with the Stat3 reporter, pLucTKS3, or the Stat3-dependent VEGF promoter-driven luciferase reporter (pGL2-VEGF-Luc) (Niu et al., 2002) following the activation of Stat3 by v-Src (Turkson et al., 1998) and the treatment with PLATINUM-401 (FIG. 3B, upper two panels). Taken together with the results in FIG. 1, these findings indicate that PLATINUM-401 blocks the binding of activated Stat3 to its responsive elements in the promoters of target genes. Moreover, in a time- and dose-dependent manner, PLATINUM-401 inhibits the constitutive or ligand-induced activation of Stat3 DNA-binding activity (FIG. 3C), as well as tyrosine phosphorylation in mouse fibroblasts (FIG. 3D and data not shown). The inventors noted IL-6-induced Stat3 activation was inhibited by PLATINUM-401 as early as 30 min (FIG. 3C, lower panel), while the inhibition of constitutively-active Stat3 in v-Src-transformed NIH3T3/v-Src by PLATINUM-401 required longer than 12 h to be significant (data not shown). Changes in Stat3 protein levels were minimal. In contrast, the platinum compound has no inhibitory effects on the induction of Stat3-independent NFκB promoter-driven (NFκB-Luc) or c-fos promoter-driven (pLucSRE) luciferase reporter activity in transient transfection studies in mouse fibroblasts (FIG. 3B, lower two panels). Results together indicate that at the 5-10 µM PLATINUM-401 that inhibits intracellular Stat3 signaling, there is no observable non-specific effect on non-Stat3 related pathways investigated here. These findings together demonstrate that PLATINUM-401 selectively represses the tyrosine phosphorylation and DNA-binding activity of Stat3, as well as the transcriptional regulation in cells by Stat3. PLATINUM-401 was next evaluated for effects on Stat3-mediated v-Src transformation (Turkson et al., 1998; Bromberg et al., 1998; Turkson et al., 1999). In soft-agar growth assays of v-Src-transformed (NIH3T3/v-Src) fibroblasts, results show that treatment of cells with PLATINUM-401 strongly suppresses growth (FIG. 4, left panel). In contrast, similar treatment of v-Ras-transformed (NIH3T3/v-Ras) fibroblasts growing in soft agar only partially inhibits growth (FIG. 4, right panel). These findings are consistent with inhibition of constitutively-active Stat3 by PLATINUM-401 and attenuation of growth of v-Src transformed cells, and show that the PLATINUM-401 inhibitory effect is selective against cells harboring constitutively-active Stat3.

Example 6-PLATINUM-401-Induced Block of Cell Cycle Progression and Proliferation The inventors further examined the biological effects of PLATINUM-401 and determined whether any changes might correlate with the inhibition of constitutively-active Stat3. Normal NIH3T3 and their v-Src-transformed counterparts, human breast cancer cell lines harboring constitutively-active Stat3 (MDA-MB-435, MDA-MB-231, and MDA-MB-468) and those that do not harbor Stat3 activity (MDA-MB-453 and MCF-7), as well as a human non-small cell lung cancer cell line (A549), a human prostate cancer cell line (DU145) and a murine multiple myeloma cell line (5TGM1), all of which harbor constitutively-active Stat3 (Garcia et al., 2001; Mora et al., 2002; Song et al., 2003), were treated with or without PLATINUM-401 for 24 h. Cells were then harvested for nuclear extract preparation and in vitro Stat3 DNA-binding activity assay with EMSA analysis, or processed for cell proliferation and cell cycle analysis by flow cytometry.

Figure 5A:
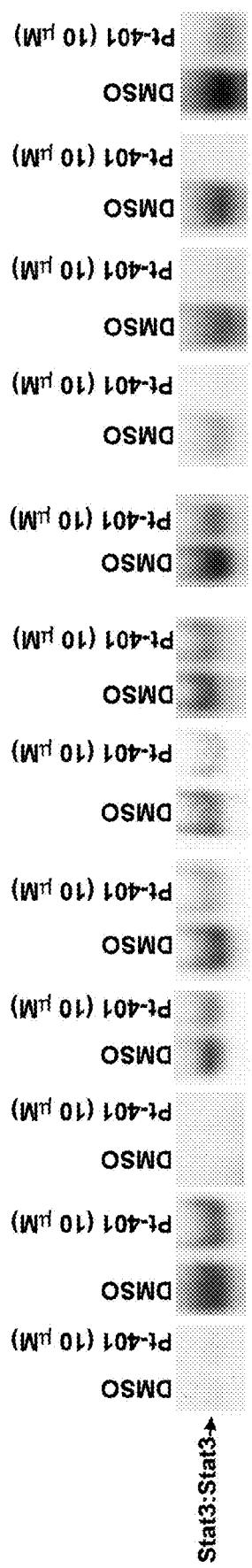
FIGS. 5A and 5B. Evaluation for effects of PLATINUM-401 on cellular constitutive Stat3 activation and cell proliferation. Normal or malignant cells were treated with or without PLATINUM-401 and nuclear extracts were prepared for Stat3 DNA-binding activity assay with hSIE probe, or cells were processed for nuclear Ki67 immunohistochemistry.

EMSA analysis of Stat3 DNA-binding activity in nuclear extracts prepared from malignant cells harboring constitutively-active Stat3 and treated with PLATINUM-401 reveals significant inhibition of constitutive activation of Stat3 in those cells (FIG. 5A). These observations support the inhibition of Stat3 transcriptional activity (FIG. 3) and together indicate that PLATINUM-401 selectively blocks constitutive activation of Stat3 signaling in diverse cell types. Normal NIH3T3 fibroblasts and human the breast cancer cell line, MDA-MB-453, do not harbor constitutively-active Stat3 (FIG. 5A).

Figure 5B:
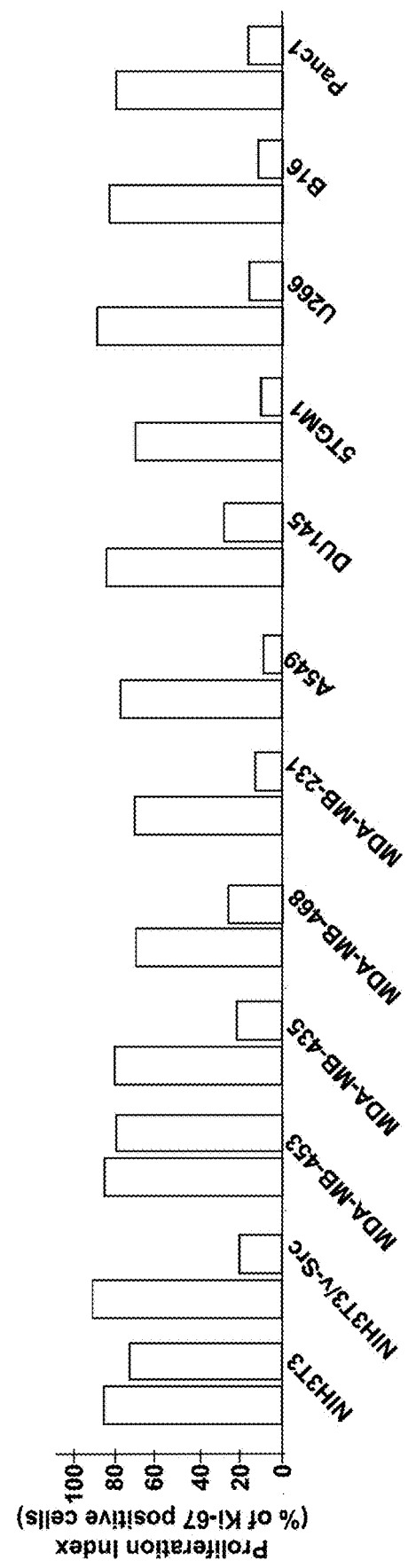

Changes in cell proliferation induced by treatment with PLATINUM-401 were assayed in terms of Ki67 proliferation index by immunohistochemistry. The presence of Ki-67 nuclear staining was calculated as the percent positive tumor cells in relation to the total number of cells. In contrast to the lack of effect of PLATINUM-401 on the proliferation of normal NIH 3T3 fibroblasts or the human breast cancer cell line MDA-MB-453 that do not harbor persistent Stat3 activity, treatment with PLATINUM-401 causes significant decreases in Ki67 nuclear staining for the malignant cells harboring constitutively-active Stat3 (FIG. 5B), which correlates with inhibition of Stat3 activity (FIG. 5A).

Figure 6:
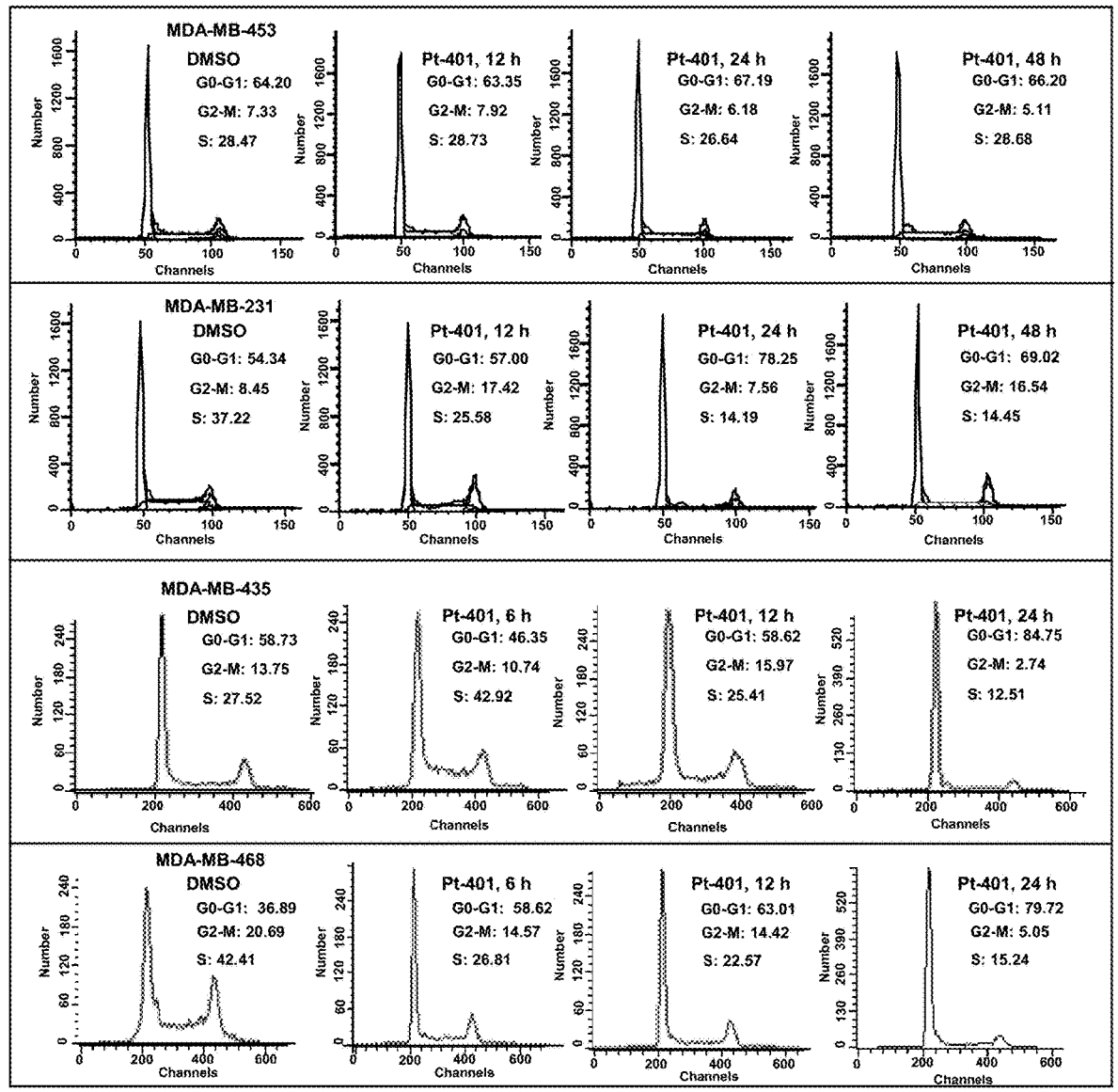
FIG. 6. Analysis of relative cellular DNA content using BrdU labeling and flow cytometry. Relative DNA content of human breast cancer cell lines following treatment with or without PLATINUM-401 was analyzed by BrdU incorporation and flow cytometry. The population of cells determined from the relative DNA content is shown in each panel for each treatment condition. Results are the representative of 3 independent determinations.

In flow cytometric analyses for cell cycle changes in PLATINUM-401-treated and untreated (control) cells exposed to BrdU, results show that the breast cancer cell line, MDA-MB-231, is arrested at $G_0/G_1$ phase following PLATINUM-401 treatment (FIG. 6). A significant decrease in S phase cells is also observed, which parallels the drop in DNA synthesis as judged from the level of incorporation of BrdU, and persists up to 48 h. Similar results are observed after 6 h of PLATINUM-401-treatment of the breast cancer cell line, MDA-MB-468 (FIG. 6, and data not shown). In the case of the MDA-MB-435 cell line, similar observations are made following 24 h treatment (FIG. 6). In contrast, no significant change in cell cycle profile is observed when the breast cancer cell line MDA-MB-453 that does not harbor constitutively-active Stat3 is treated with PLATINUM-401 (FIG. 6). These findings together show that malignant cells harboring persistently-elevated Stat3 activity are more sensitive to PLATINUM-401 than cells that do not, consistent with the ability of PLATINUM-401 to inhibit constitutively-active Stat3 and its biological functions.

Example 7-PLATINUM-401-Mediated Apoptosis of Malignant Cells

Figure 7A:
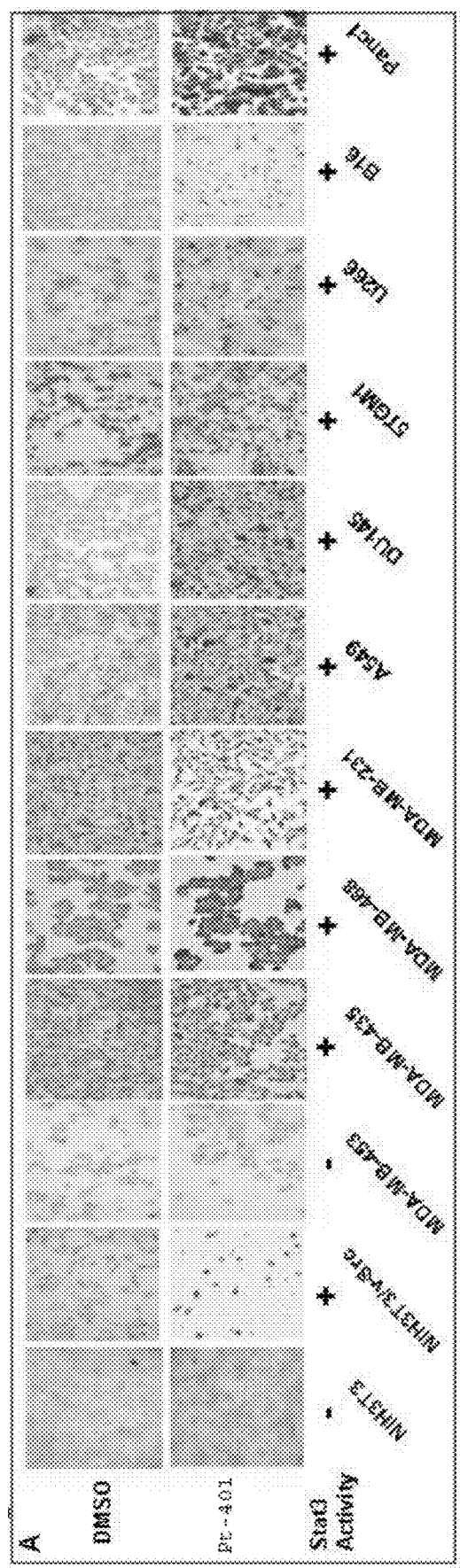
FIGS. 7A-7C. TUNEL analysis of PLATINUM-401-mediated apoptosis.
Figure 7B:
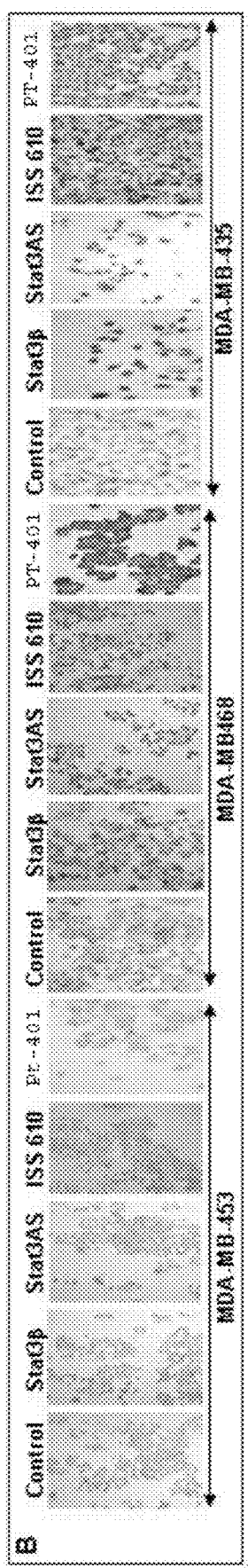

Malignant cells harboring persistent Stat3 signaling and those that do not were examined for evidence of apoptosis following treatment with PLATINUM-401. Cells were analyzed for DNA-strand breaks by TUNEL staining. Significant TUNEL staining was detected in v-Src-transformed fibroblasts (NIH3T3/v-Src), human breast carcinoma cell lines (MDA-MB-435, MDA-MB-468, MDA-MD-231), human non-small cell lung cancer cell line (A549), human prostate carcinoma cell line (DU145), multiple myeloma cell lines 5TGM1 (mouse) and U266 (human), mouse melanoma cell line (B16), and human pancreatic cancer cell line (Panc1), all of which harbor constitutively-active Stat3, following treatment with PLATINUM-401 (FIG. 7). In contrast, no TUNEL staining was observed in control (DMSO-treated) cells, or in mouse fibroblast cells (NIH3T3) and human breast cancer cells (MDA-MB-453) that do not contain aberrant Stat3 activity and were treated with PLATINUM-401 (FIG. 7). The incidence of apoptosis correlated with the prevalence of constitutively-active Stat3 in malignant cells (FIG. 7, lower panel). Moreover, the incidence of apoptosis by PLATINUM-401 in breast cancer cell lines (MDA-MB-468 and MDA-MB-435) harboring constitutively-active Stat3 compares favorably to that induced by other previously investigated Stat3 inhibitory approaches, such as Stat3β (Garcia et al., 2001), Stat3 antisense (Stat3AS) (Mora et al., 2002), peptidomimetic inhibitor of Stat3 (ISS 610) (FIG. 7B) (Turkson et al., 2004c), and contrasts with the absence of apoptosis in breast cancer cell line, MDA-MB-453 that lacks constitutively-active Stat3. These results indicate differences in sensitivity of cells to PLATINUM-401, which are dependent on the activation status of Stat3 inside cells. The susceptible malignant cells are those that harbor constitutively-active Stat3, which undergo cell cycle arrest and apoptosis in response to PLATINUM-401, consistent with previous reports (Catlett-Falcone et al., 1999; Grandis et al., 2000; Garcia et al., 2001; Epling-Burnette et al., 2001; Bowman et al., 2000b; Turkson et al., 2004b; Mora et al., 2002).

Figure 7C:
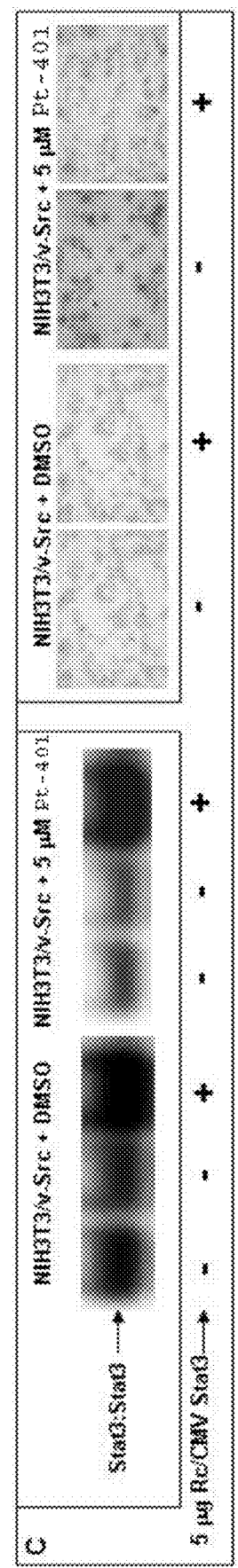

Example 8—In Vivo Overexpression of Stat3 Protein Affects PLATINUM-401 Activity and Effect To further elucidate the interaction between Stat3 and PLATINUM-401, v-Src-transformed mouse fibroblasts were transfected with Stat3 protein and then used to investigate PLATINUM-401 activity. The transfection of wild-type Stat3 into the v-Src-transformed fibroblasts results in higher Stat3 DNA-binding activity over that of parentals, as measured by in vitro DNA-binding activity and EMSA analysis (FIG. 7C, left panel, lanes 3 and 6 versus 1 and 2). This is due to the increased expression of Stat3 protein and the consequent phosphorylation by oncogenic Src tyrosine kinase that is present in these cells. EMSA analysis of nuclear extracts prepared from parental, mock-transfected cells and treated with PLATINUM-401 show significant reduction in constitutively-active Stat3 DNA-binding activity (FIG. 7C, left panel, lanes 4 and 5 versus 1 and 2), as previously observed (FIG. 3C, top panel, FIG. 5A, lanes 3 and 4). In contrast, EMSA analysis show that cells transfected with exogenous wild-type Stat3 and treated with PLATINUM-401 show no significant reduction in constitutively-active Stat3 DNA-binding activity (FIG. 7C left panel, lane 6 versus 3). This finding is consistent with data from the in vitro DNA-binding assay (FIG. 1C (ii)) and together indicates that the presence of higher Stat3 protein, either as a monomer or dimer, diminishes the relative potency of PLATINUM-401, thus further confirming that PLATINUM-401 interacts with Stat3 protein. Moreover, in diminishing the effect of PLATINUM-401 on Stat3 DNA-binding activity, studies show that the overexpression of Stat3 in v-Src-transformed mouse fibroblasts minimizes the extent of PLATINUM-401-mediated apoptosis (FIG. 7C, right panel, two far right images). Finally, this finding is important in suggesting that the potency of direct inhibitors of Stat3 activation as therapeutics for tumors harboring constitutively-active Stat3 is influenced by the expression levels of the Stat3 protein.

Example 9-PLATINUM-401 Represses Induction of Bcl-xL and Cyclin D1

Figure 8A:
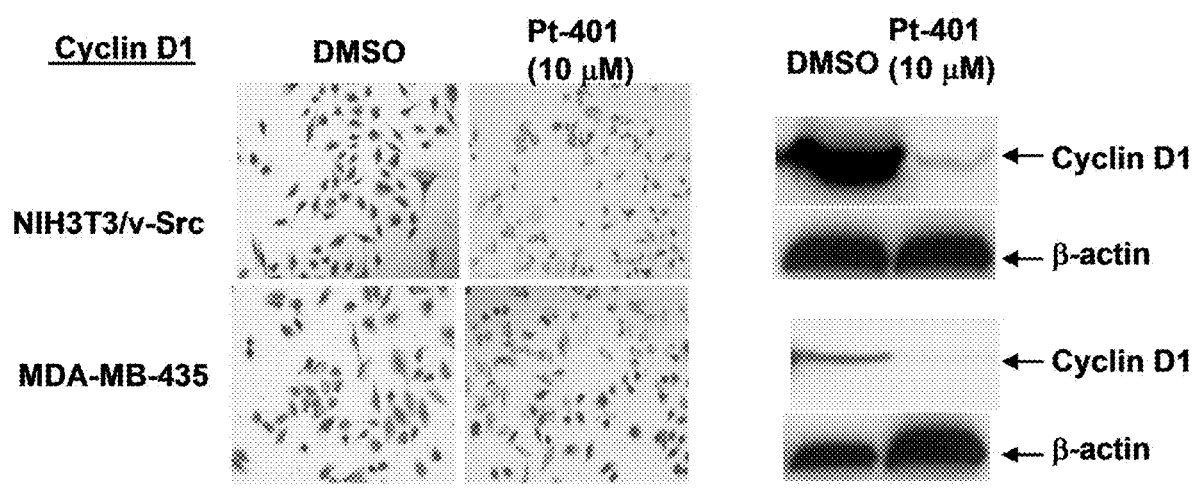
FIGS. 8A and 8B. Inhibition of Cyclin D1 and Bcl-xL induction by PLATINUM-401. Viral Src-transformed fibroblasts (NIH3T3/v-Src) and human breast cancer cell line MDA-MB-435 that contain constitutively-activated Stat3 were treated with or without platinum complex for 48 h. Cells were processed for immunohistochemistry, or cell lysates were prepared from cells and subjected to 5% PAGE and Western blot analysis, as indicated in "Materials and Methods.
Figure 8B:
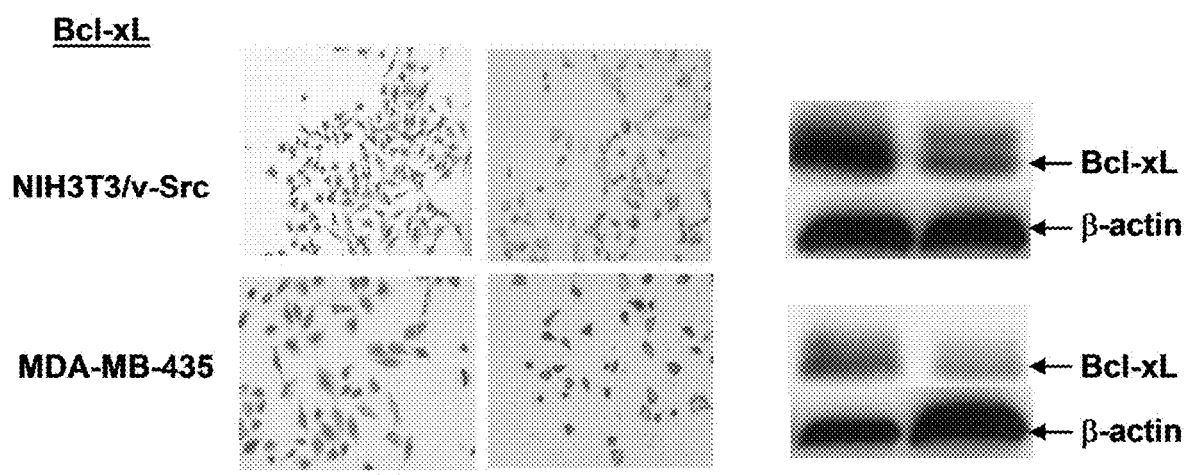
Figure 9:
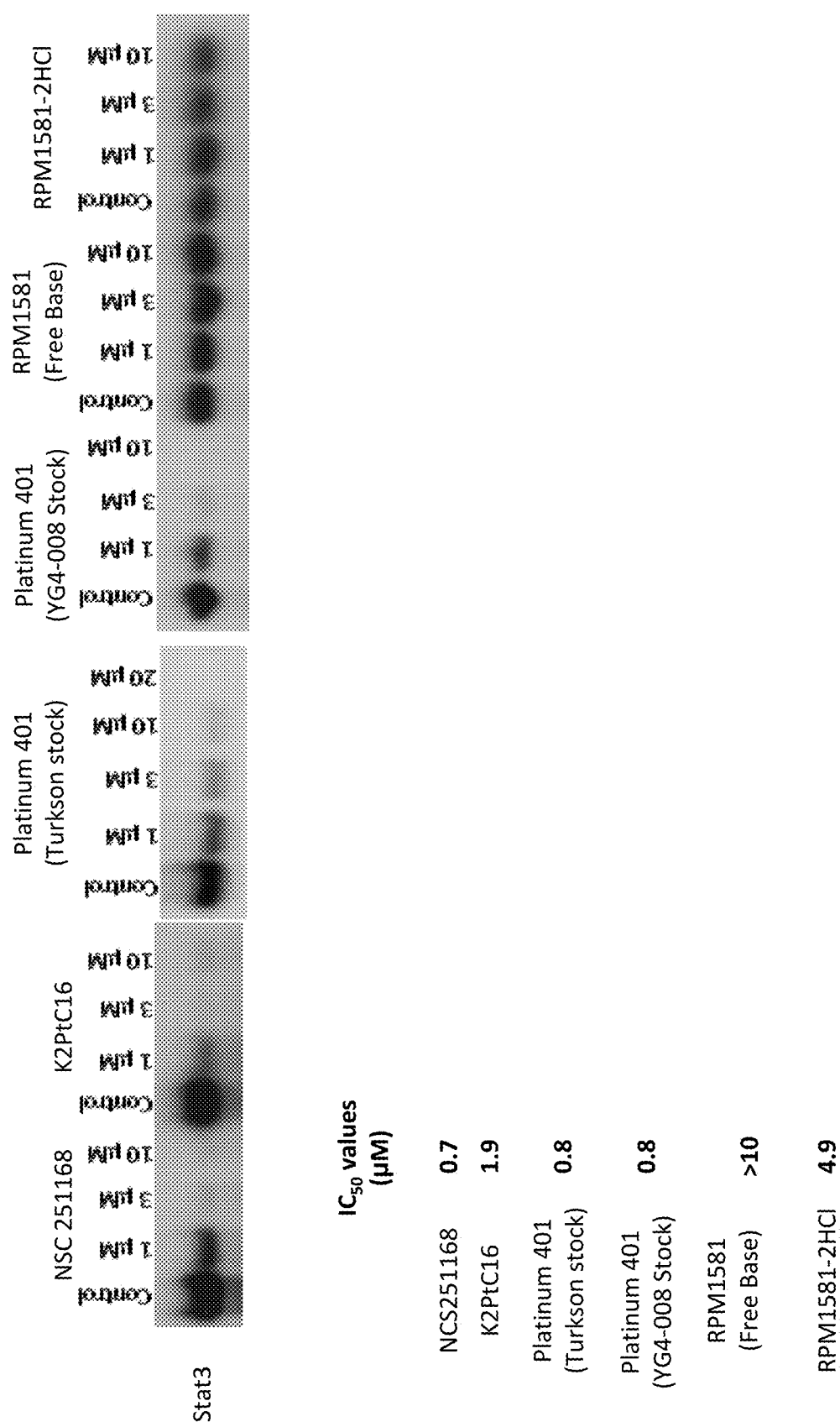
FIG. 9. STAT3 DNA-binding activity/EMSA assay in vitro and the effects of compounds. Nuclear extracts or cell lysates containing activated Stat3 were treated with or without the indicated concentrations of NSC 251168, platinum complex K2PtCl6, PLATINUM-401 (supplied by Dr. Turkson), PLATINUM-401 (supplied by Dr. Lawrence as described in Example 10 herein), RPM1581 (free base) (supplied by Dr. Lawrence as described in Example 10 herein and also designated as YL5-108), or RPM1581-2HCl (salt form) (supplied by Dr. Lawrence), for 30 min at room temperature prior to incubation with radiolabeled oligonucleotide probes, and subjected to EMSA analysis.
Figure 10:
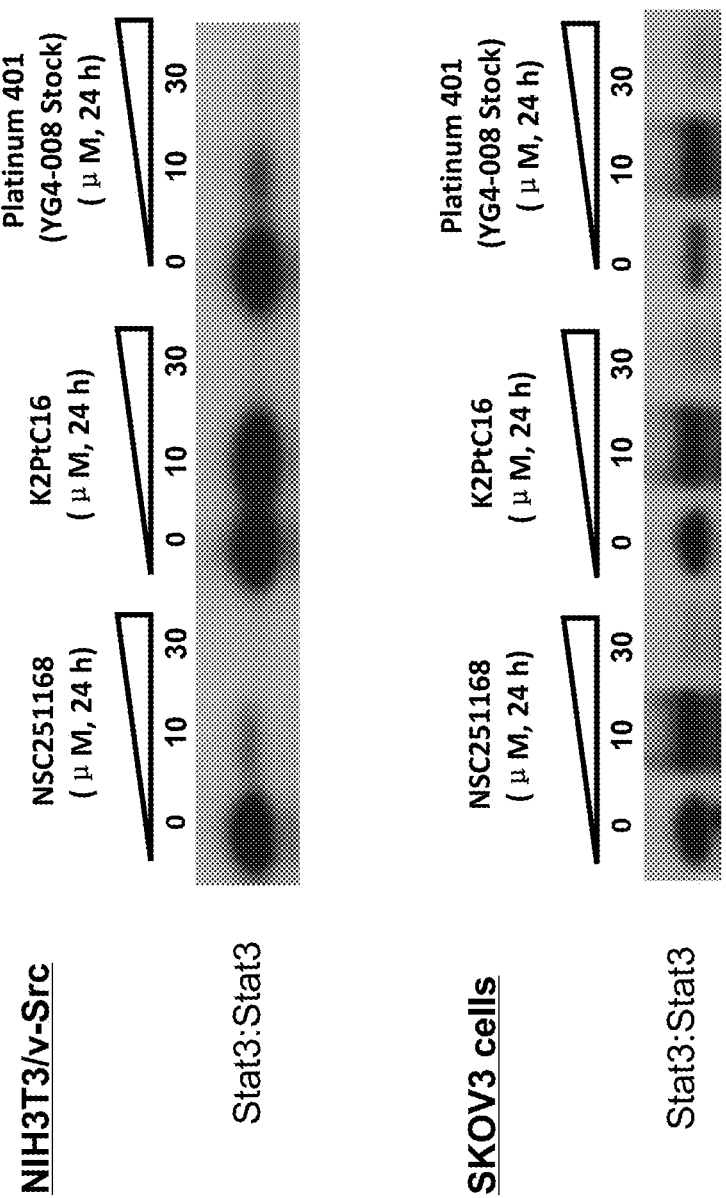
FIG. 10. Inhibition of Stat3 activation in tumor cells. In each case, NIH3T3/v-Src or human SKOV3 cells were treated with 0, 10, or 30 micromolar concentrations of NSC 251168, platinum complex K2PtCl6, or PLATINUM-401 (supplied by Dr. Lawrence as described in Example 10 herein) drug for 24 hr, and Stat3 activation assayed by EMSA.

To investigate the molecular changes downstream from Stat3 that may contribute to the biological responses induced by PLATINUM-401, in situ detection and Western blot analyses were performed for cell cycle and apoptosis regulators. Results show that Cyclin D1 was significantly diminished in v-Src-transformed mouse fibroblasts (NIH3T3/v-Src) and a human breast cancer cell line (MDA-MB-435) in response to PLATINUM-401-induced inhibition of Stat3 activation (FIG. 8). Similar observations were made for the anti-apoptotic Bcl-xL protein in both malignant cell lines, which harbor constitutively-active Stat3, following treatment with PLATINUM-401 (FIG. 8). These findings parallel the cell cycle or proliferation changes and the induction of apoptosis by the PLATINUM-401 treatment (FIGS. 5, 6, and 7), and indicate that inhibition of constitutively-active Stat3 by PLATINUM-401 blocks Cyclin D1 and Bcl-xL induction.

Example 10-Synthesis of 10 g Sample of PLATINUM-401

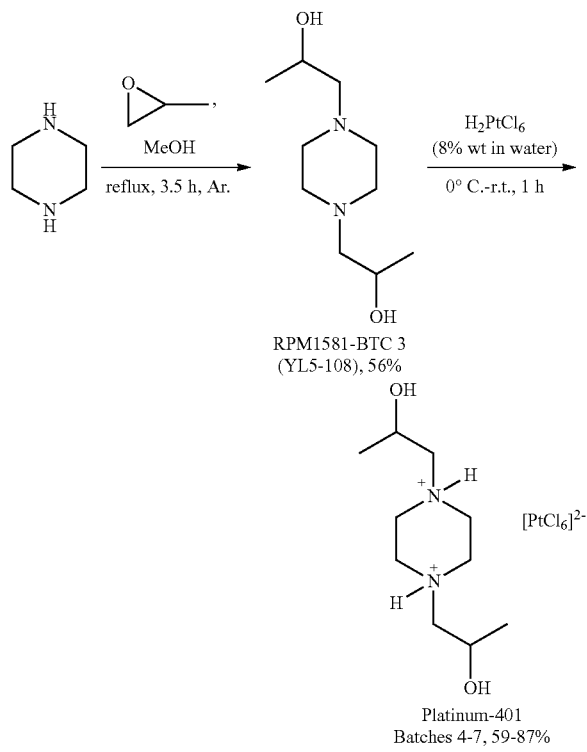

Synthesis of RPM1581.

A mixture of piperazine (Fisher/Acros AC13129) (28.1 g, 0.326 mol), and propylene oxide (Fisher/Acros AC14962-0010)(41.47 g, 0.714 mol) in anhydrous methanol (32 mL) in a 250 mL round bottom flask was refluxed under argon for 3.5 h. After cooling to room temperature, the reaction mixture was allowed to stand at room temperature for overnight. The precipitate was filtered, washed with cold methanol (20 mL), then diethyl ether (20 mL) providing the product (28.16 g). The filtrate was concentrated and slurried with MeOH, filtered and dried to provide additional pure product (8.97 g). The solids were combined to provide RPM1581-BTC3 (37.13 g, 56%) as a white solid.

Synthesis of PLATINUM-401.

Chloroplatinic acid ($H_2PtCl_6$, Aldrich cat.#262587) (13.11 mL of 8 wt % in water, 2.56 mmol) was added over 5 minutes to RPM1581-BTC 3 (0.518 g, 2.56 mmol) in a flask cooled in an ice water bath. The reaction mixture was clear after approximately 1 mL of chloroplatinic acid solution was added (i.e., the RPM1581 dissolved). An orange precipitate formed while the addition of the remaining RPM1581 was ongoing. The reaction mixture was stirred in r.t. for another hour. The orange precipitate was filtered and washed with water (20 mL×4). The solid was dried under high vacuum (5 torr) at 80° C. for 3 days to provide pure PLATINUM-401 (1.180 g, 76%) as an orange solid.

PLATINUM-401 batch 5: 2× scale gave (2.72 g, 87%)
PLATINUM-401 batch 6: 4× scale gave (4.66 g, 74%)
PLATINUM-401 batch 7: 4× scale gave (3.74 g, 59%)
PLATINUM-401 Batches 4, 5, 6, 7 were combined, thoroughly mixed, and dried under high vacuum (5 torr)) at 80° C. overnight. Elemental Analysis: Found C, 19.56%; H, 3.91; Cl, 35.28, N, 4.41. $C_{10}H_{24}Cl_6N_2O_2Pt$ requires C, 19.62%; H, 3.95; Cl, 34.75; N, 4.58.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Akira, S. (2000) Oncogene 19, 2607-2611
Allain, P., Heudi, O., Cailleux, A., Le Bouil, A., Larra, F., Boisdron-Celle, M., and Gamelin, E. (2000) Drug. Metab. Dispos. 28, 1379-1384
Becker, S., Groner, B., and Muller, C. W. (1998) Nature 394, 145-151
Bose, R. N. (2002) Mini. Rev. Med. Chem. 2, 103-111.
Bowman, T., Garcia, R., Turkson, J., and Jove, R. (2000a) Oncogene 19, 2474-2488
Bowman, T., Broome, M., Sinibaldi, N., Wharton, W., Pledger, W. J., Sedivy, J., Irby, R., Yeatman, T., Courneidge, S. A., and Jove, R. (2000b) Proc. Natl. Acad. Sci. USA 98, 7319-7324
Bromberg, J. (2000) Breast Cancer Res. 2(2), 86-90.
Bromberg, J. F., Horvath, C. M., Besser, D., Lathem, W. W., and Darnell, J. E., Jr. (1998) Mol. Cell. Biol. 18, 2553-2558
Bromberg, J. F., Horvath, C. M., Wen, Z., Schreiber, R. D., and Darnell, J. E., Jr. (1996) Proc. Natl. Acad. Sci. USA 93, 7673-7678
Bromberg, J. F., Wrzeszczynska, M. H., Devgan, G., Zhao, Y., Pestell, R. G., Albanese, C., and Darnell, J. E., Jr. (1999) Cell 98, 295-303
Buettner, R., Mora, L. B., and Jove, R. (2002) Clin. Cancer Res. 8, 945-954
Catlett-Falcone, R., Landowski, T. H., Oshiro, M. M., Turkson, J., Levitzki, A., Savino, R., Ciliberto, G., Moscinski, L., Fernandez-Luna, J. L., Nuñez, G., Dalton, W. S., and Jove, R. (1999) Immunity 10, 105-115
Coffer, P. J., Koenderman, L., and de Groot, R. P. (2000) Oncogene 19, 2511-2522
Darnell, J. E., Jr. (1997) Science 277, 1630-1635
Darnell, J. E., Jr. (2002) Nat. Rev. Cancer 2, 740-749
Darnell, J. E., Jr., Kerr, I. M., and Stark, G. R. (1994) Science 264, 1415-1421

Epling-Burnette, P. K., Lui, J. H., Catlette-Falcone, R., Turkson, J., Oshiro, M., Kothapalli, R., Li, Y., Wang, J.-M., Yang-Yen, H.-F., Karras, J., Jove, R., and Loughran, T. P., Jr. (2001) J. Clin. Invest. 107, 351-362

Fukada, T., Hibi, M., Yamanaka, Y., Takahashi-Tezuka, M., Fujitani, Y., Yamaguchi, T., Nakajima, K., and Hirano, T. (1996) Immunity 5, 449-460

Garcia, R., Bowman, T. L., Niu, G., Yu, H., Minton, S., Muro-Cacho, C. A., Cox, C. E., Falcone, R., Fairclough, R., Parson, S., Laudano, A., Gazit, A., Levitzki, A., Kraker, A., and Jove, R. (2001) Oncogene 20, 2499-2513

Garcia, R., Yu, C. L., Hudnall, A., Catlett, R., Nelson, K. L., Smithgall, T., Fujita, D. J., Ethier, S. P., and Jove, R. (1997) Cell Growth Diff. 8, 1267-1276

Gouilleux, F., Moritz, D., Humar, M., Moriggl, R., Berchtold, S., and Groner, B. (1995) Endocrinology 136, 5700-5708

Grandis, J. R., Drenning, S. D., Zeng, Q., Watkins, S. C., Melhem, M. F., Endo, S., Johnson, D. E., Huang, L., He, Y., and Kim, J. D. (2000) Proc. Natl. Acad. Sci. USA 97, 4227-4232

Heudi, O., Brisset, H., Cailleux, A., and Allain, P. (2001) Int. J. Clin. Pharmacol. Ther. 39, 344-349

Heudi, O., Mercier-Jobard, S., Cailleux, A., and Allain, P. (1999) Biopharm. Drug Dispos. 20, 107-116

Hirano, T., Ishihara, K., and Hibi, M. (2000) Oncogene 19, 2548-2556

Hussain, S. F., Kong, L-Y., Jordan, J. et al. (2007) Cancer Res. 67, 9630-9636

Johnson, P. J., Coussens, P. M., Danko, A. V., and Shalloway, D. (1985) Mol. Cell. Biol. 5, 1073-1083

Karras, J., McKay, R., Lu, T., Pych, J., Frank, D., Rothstein, T., and Monia, B. (2000) Cell. Immunol. 202, 124-135

Kotenko, S. V., and Pestka, S. (2000) Oncogene 19, 2557-2565

Lin, T. S., Mahajan, S., and Frank, D. A. (2000) Oncogene 19, 2496-2504

Mora, L. B., Buettner, R., Seigne, J., Diaz, J., Ahmad, N., Garcia, R., Bowman, T., Falcone, R., Fairclough, R., Cantor, A., Muro-Cacho, C., Livingston, S., Karras, J., Pow-Sang, J., and Jove, R. (2002) Cancer Res 62, 6659-6666.

Nielsen, M., Kaestel, C. G., Eriksen, K. W., Woetmann, A., Stokkedal, T., Kaltoft, K., Geisler, C., Ropke, C., and Odum, N. (1999) Leukemia 13, 735-738

Nielsen, M., Kaltoft, K., Nordahl, M., Ropke, C., Geisler, C., Mustelin, T., Dobson, P., Svejgaard, A., and Odum, N. (1997) Proc. Natl. Acad. Sci. USA 94, 6764-6769

Niu, G., Heller, R., Catlett-Falcone, R., Coppola, D., Jaroszeski, M., Dalton, W., Jove, R., and Yu, H. (1999) Cancer Res. 59, 5059-5063

Niu, G., Wright, K. L., Huang, M., Song, L., Haura, E., Turkson, J., Zhang, S., Wang, T., Sinibaldi, D., Coppola, D., Heller, R., Ellis, L. M., Karras, J., Bromberg, J., Pardoll, D., Jove, R., and Yu, H. (2002) Oncogene 21, 2000-2008.

Oshiro, M. M., Landowski, T. H., Catlett-Falcone, R., Hazlehurst, L. A., Huang, M., Jove, R., and Dalton, W. S. (2001) Clin. Cancer Res. 7, 4262-4271

Oyajobi, B. O., Franchin, G., Williams, P. J., Pulkrabek, D., Gupta, A., Munoz, S., Grubbs, B., Zhao, M., Chen, D., Sherry, B., and Mundy, G. R. (2003) Blood 102, 311-319.

Perez, J. M., Kelland, L. R., Montero, E. I., Boxall, F. E., Fuertes, M. A., Alonso, C., and Navarro-Ranninger, C. (2003) Mol. Pharmacol. 63, 933-944

Persons, D. L., Yazlovitskaya, E. M., Cui, W., and Pelling, J. C. (1999) Clin. Cancer. Res. 5, 1007-1014.

Sanchez-Perez, I., Murguia, J. R., and Perona, R. (1998) Oncogene 16, 533-540.

Schindler, C., and Darnell, J. E., Jr. (1995) Annu. Rev. Biochem. 64, 621-651

Seidel, H. M., Milocco, L. H., Lamb, P., Darnell, J. E., Jr., Stein, R. B., and Rosen, J. (1995) Proc. Natl. Acad. Sci. USA 92, 3041-3045

Siddik, Z. H. (2003) Oncogene 22, 7265-7279.

Siddiquee, K. et al. (2007) PNAS, 104(18):7391-7396.

Sinibaldi, N., Wharton, W., Turkson, J., Bowman, T., Pledger, W. J., and Jove, R. (2000) Oncogene 19, 5419-5427

Smithgall, T. E., Briggs, S. D., Schreiner, S., Lerner, E. C., Cheng, H., and Wilson, M. B. (2000) Oncogene 19, 2612-2618

Song, H., Wang, R., Wang, S. and Lin, J. (2005) PNAS 102(13), 4700-4705.

Song, J. I., and Grandis, J. R. (2000) Oncogene 19, 2489-2495

Song, L., Turkson, J., Karras, J. G., Jove, R., and Haura, E. B. (2003) Oncogene 22, 4150-4165

Stark, G. R., Kerr, I. M., Williams, B. R., Silverman, R. H., and Schreiber, R. D. (1998) Annu. Rev. Biochem. 67, 227-264

Trynda-Lemiesz, L., and Luczkowski, M. (2004) J. Inorg. Biochem. 98, 1851-1856

Trynda-Lemiesz, L., Kozlowski, H., and Keppler, B. K. (1999) J. Inorg. Biochem. 77, 141-146

Turkson, J., and Jove, R. (2000) Oncogene 19, 6613-6626

Turkson, J., Bowman, T., Adnane, J., Zhang, Y., Djeu, J. Y., Sekharam, M., Frank, D. A., Holzman, L. B., Wu, J., Sebti, S., and Jove, R. (1999) Mol. Cell. Biol. 19, 7519-7528

Turkson, J., Bowman, T., Garcia, R., Caldenhoven, E., De Groot, R. P., and Jove, R. (1998) Mol. Cell. Biol. 18, 2545-2552

Turkson, J., Ryan, D., Kim, J. S., Zhang, Y., Chen, Z., Haura, E., Laudano, A., Sebti, S., Hamilton, A. D., and Jove, R. (2001) J. Biol. Chem. 276, 45443-45455

Turkson, J. (2004a) Expert Opin. Ther. Targets 8, 409-422.

Turkson, J., Zhang, S., Palmer, J., Kay, H., Stanko, J., Mora, L. B., Sebti, S., Yu, H., and Jove, R. (2004b) Mol. Cancer Ther. 3, 1533-1542

Turkson, J., Kim, J. S., Zhang, S., Yuan, J., Huang, M., Glenn, M., Haura, E., Sebti, S., Hamilton, A. D., and Jove, R. (2004c) Mol. Cancer Ther. 3, 261-269

Ueki, N., Seki, N., Yano, K., Saito, T., Masuho, Y., and Muramatsu, M. (1999) J. Human Genetics 44, 193-196

Wagner, B. J., Hayes, T. E., Hoban, C. J., and Cochran, B. H. (1990) EMBO J. 9, 4477-4484

Wang, T., Niu, G., Kortylewski, M., Burdelya, L., Shain, K., Zhang, S., Bhattacharya, R., Gabrilovich, D., Heller, R., Coppola, D., Dalton, W., Jove, R., Pardoll, D., and Yu, H. (2004a) Nat. Med. 10, 48-54

Wang, G., Reed, E., and Li, Q. Q. (2004b) Oncol. Rep. 12, 955-965

Yamauchi, K., Holt, K., and Pessin, J. E. (1993) J. Biol. Chem. 268, 14597-14600

Yu, C. L., Meyer, D. J., Campbell, G. S., Larner, A. C., Carter-Su, C., Schwartz, J., and Jove, R. (1995) Science 269, 81-83

Yu, H., and Jove, R. (2004) Nat. Rev. Cancer 4, 97-105

Zhang, D., Sun, M., Samols, D., and Kushner, I. (1996) J. Biol. Chem. 271, 9503-9509

Zhang, Y., Turkson, J., Carter-Su, C., Smithgall, T., Levitzki, A., Kraker, A., Krolewski, J. J., Medveczky, P., and Jove, R. (2000) J. Biol. Chem. 275, 24935-24944

We claim:

1. A method for treating a subject having a disorder or condition associated with aberrant or excessive Stat3 activity or interaction in a cell, comprising determining that the disorder or condition is associated with aberrant or excessive Stat3 activity or interaction in a cell; and, after said determining, administering an effective amount of a compound to the subject, wherein the compound has the structure shown in formula I, formula II, or formula III:

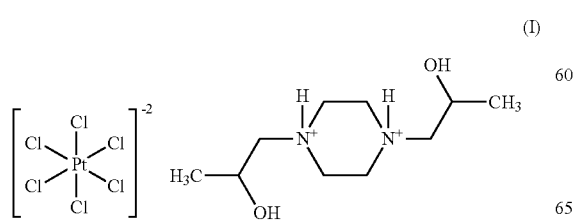

(I)

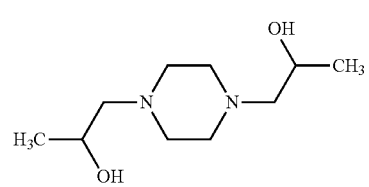

(II)

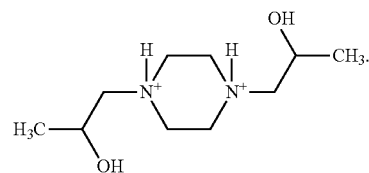

(III)

2. The method of claim 1, wherein the disorder is an oncological disorder.

3. The method of claim 1, wherein said determining comprises measuring a level of Stat3 activity or interaction in a biological sample collected from the subject and comparing the measured level to a reference level of Stat3 activity or interaction.

4. The method of claim 1, wherein the compound is administered to the subject in a composition comprising the compound and a carrier, buffer, adjuvant, or a combination of two or more of the foregoing.

5. The method of claim 1, wherein the subject is a mammal.

6. The method of claim 1, wherein the subject is a non-human mammal.

7. The method of claim 1, wherein the subject is human.

8. A method for inducing apoptosis in a cell aberrantly or constitutively expressing active Stat3, comprising determining that the cell or a representative cell aberrantly or constitutively expresses active Stat3; and, after said determining, contacting the cell with an effective amount of a compound to the subject, wherein the compound has the structure shown in formula I, formula II, or formula III:

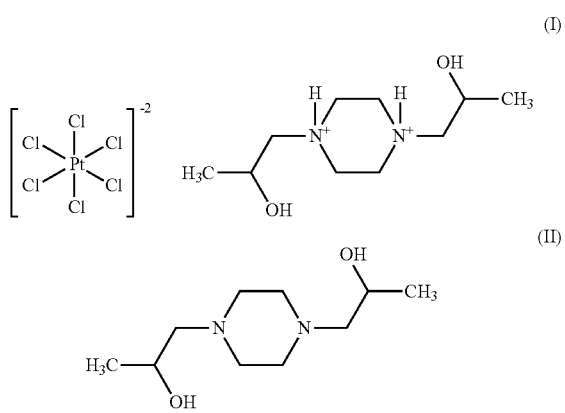

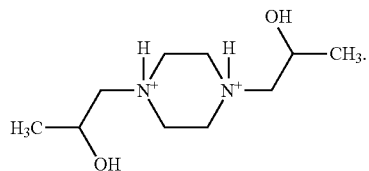

9. The method of claim 8, wherein the cell is a malignant cell.

10. The method of claim 8, wherein said determining comprises measuring a level of Stat3 activity or interaction in the cell or representative cell and comparing the measured level to a reference level of Stat3 activity or interaction.

11. The method of claim 8, wherein said contacting comprises contacting the cell with a composition comprising the compound and a carrier, buffer, adjuvant, or a combination of two or more of the foregoing.

12. The method of claim 8, wherein said contacting is carried out in vitro.

13. The method of claim 8, wherein said contacting is carried out in vivo.

14. The method of claim 13, wherein said contacting comprises administering the effective amount of the compound to a human.

15. A method for screening and/or diagnosing an oncological condition or disorder using the compound of claim 1, wherein the condition or disorder is associated with constitutive active Stat3 expression or active Stat3 overexpression in a cell, wherein the method comprises contacting a cell with the compound; and observing the cell for induction of apoptosis.

* * * * *

UNITED STATES PATENT AND TRADEMARK OFFICE
CERTIFICATE OF CORRECTION

PATENT NO. : 10,813,927 B2  
APPLICATION NO. : 15/978499  
DATED : October 27, 2020  
INVENTOR(S) : Said M. Sebti, Nicholas J. Lawrence and James Turkson Page 1 of 1

It is certified that error appears in the above-identified patent and that said Letters Patent is hereby corrected as shown below:

In the Specification

Column 28,
Lines 7-8, "(5'-GCTCCAGCATCTGCTGCTTC-3')," should read --(5'-GCTCCAGCATCTGCTGCTTC-3')--.

Column 32,
Line 4, "3-gal" should read --β-gal--.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*